(12) United States Patent
Mirkin et al.

(10) Patent No.: US 12,319,711 B2
(45) Date of Patent: Jun. 3, 2025

(54) SPHERICAL NUCLEIC ACIDS WITH TAILORED AND ACTIVE PROTEIN CORONAE

(71) Applicant: NORTHWESTERN UNIVERSITY, Evanston, IL (US)

(72) Inventors: Chad A. Mirkin, Wilmette, IL (US); Wuliang Zhang, Evanston, IL (US); Brian R. Meckes, Highland Village, TX (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 732 days.

(21) Appl. No.: 17/025,637

(22) Filed: Sep. 18, 2020

(65) Prior Publication Data

US 2021/0087221 A1    Mar. 25, 2021

Related U.S. Application Data

(60) Provisional application No. 62/903,223, filed on Sep. 20, 2019.

(51) Int. Cl.
| | | |
|---|---|---|
| C07H 21/04 | (2006.01) | |
| A61K 47/69 | (2017.01) | |
| B82Y 5/00 | (2011.01) | |
| C07H 21/02 | (2006.01) | |
| C07K 16/22 | (2006.01) | |
| C07K 16/28 | (2006.01) | |

(52) U.S. Cl.
CPC ......... *C07H 21/04* (2013.01); *A61K 47/6917* (2017.08); *C07H 21/02* (2013.01); *C07K 16/22* (2013.01); *C07K 16/2878* (2013.01); *B82Y 5/00* (2013.01)

(58) Field of Classification Search
None
See application file for complete search history.

(56) References Cited

U.S. PATENT DOCUMENTS

| | | | |
|---|---|---|---|
| 3,687,808 | A | 8/1972 | Merigan et al. |
| 4,469,863 | A | 9/1984 | Ts et al. |
| 4,476,301 | A | 10/1984 | Imbach et al. |
| 4,489,055 | A | 12/1984 | Couvreur et al. |
| 4,845,205 | A | 7/1989 | Huynh et al. |
| 4,981,957 | A | 1/1991 | Lebleu et al. |
| 5,008,050 | A | 4/1991 | Cullis et al. |
| 5,023,243 | A | 6/1991 | Tullis |
| 5,034,506 | A | 7/1991 | Summerton et al. |
| 5,118,800 | A | 6/1992 | Smith et al. |
| 5,130,302 | A | 7/1992 | Spielvogel et al. |
| 5,134,066 | A | 7/1992 | Rogers et al. |
| 5,166,315 | A | 11/1992 | Summerton et al. |
| 5,175,273 | A | 12/1992 | Bischofberger et al. |
| 5,177,196 | A | 1/1993 | Meyer et al. |
| 5,185,444 | A | 2/1993 | Summerton et al. |
| 5,188,897 | A | 2/1993 | Suhadolnik et al. |
| 5,194,599 | A | 3/1993 | Froehler et al. |
| 5,214,134 | A | 5/1993 | Weis et al. |
| 5,216,141 | A | 6/1993 | Benner |
| 5,235,033 | A | 8/1993 | Summerton et al. |
| 5,264,423 | A | 11/1993 | Cohen et al. |
| 5,264,562 | A | 11/1993 | Matteucci |
| 5,264,564 | A | 11/1993 | Matteucci |
| 5,264,618 | A | 11/1993 | Felgner et al. |
| 5,276,019 | A | 1/1994 | Cohen et al. |
| 5,278,302 | A | 1/1994 | Caruthers et al. |
| 5,286,717 | A | 2/1994 | Cohen et al. |
| 5,319,080 | A | 6/1994 | Leumann |
| 5,321,131 | A | 6/1994 | Agrawal et al. |
| 5,359,044 | A | 10/1994 | Cook et al. |
| 5,367,066 | A | 11/1994 | Urdea et al. |
| 5,393,878 | A | 2/1995 | Leumann |
| 5,399,676 | A | 3/1995 | Froehler |
| 5,405,938 | A | 4/1995 | Summerton et al. |
| 5,405,939 | A | 4/1995 | Suhadolnik et al. |
| 5,432,272 | A | 7/1995 | Benner |

(Continued)

FOREIGN PATENT DOCUMENTS

| | | |
|---|---|---|
| AU | 64763/98 A | 7/1998 |
| CA | 2787156 A1 | 7/2011 |

(Continued)

OTHER PUBLICATIONS

Zhang et al., An extremely stable and orthogonal DNA base pair with a simplified three-carbon backbone, J. Am. Chem. Soc., 127(1):74-75 (2005).

Zhang et al., Antibody-linked Spherical Nucleic Acids for Cellular Targeting, Journal of the American Chemical Society, 134 (40):16488-16491 (2012).

Zhang et al., Informational Liposomes: Complexes Derived from Cholesteryl-conjugated Oligonucleotides and Liposomes, Tetrahedron Letters, 37(35):6243-6246 (1996).

Zhang et al., PowerBLAST: a new network BLAST application for interactive or automated sequence analysis and annotation, Genome Res., 7(6):649-656 (1997).

Zhang et al., Strategy for Increasing Drug Solubility and Efficacy through Covalent Attachment to Polyvalent DNA Nanoparticle Conjugates, ACS Nano, 5(9):6962-6970 (2011).

(Continued)

*Primary Examiner* — Mark L Shibuya
(74) *Attorney, Agent, or Firm* — MARSHALL, GERSTEIN & BORUN LLP

(57) ABSTRACT

The disclosure is generally related to spherical nucleic acids (SNAs) comprising a protein corona, wherein the SNA comprises (i) a nanoparticle core and (ii) one or more oligonucleotides attached to the surface of the nanoparticle core, wherein the protein corona comprises a plurality of proteins. The disclosure also provides methods of using the same. The disclosure further provides methods of improving stability and/or extending blood circulation half-life of a spherical nucleic acid (SNA), the SNA comprising a nanoparticle core and one or more oligonucleotides attached to the surface of the nanoparticle core, the method comprising adsorbing a plurality of proteins on the surface of the SNA.

22 Claims, 8 Drawing Sheets

Specification includes a Sequence Listing.

(56) References Cited

U.S. PATENT DOCUMENTS

| | | |
|---|---|---|
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,502,177 A | 3/1996 | Matteucci et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,555 A | 10/1996 | Froehler et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,714,331 A | 2/1998 | Buchardt et al. |
| 5,719,262 A | 2/1998 | Buchardt et al. |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,747 A | 8/1998 | Schally et al. |
| 5,814,666 A | 9/1998 | Green et al. |
| 5,830,653 A | 11/1998 | Froehler et al. |
| 5,955,589 A | 9/1999 | Cook et al. |
| 6,005,096 A | 12/1999 | Matteucci et al. |
| 6,051,698 A | 4/2000 | Janjic et al. |
| 6,239,116 B1 | 5/2001 | Krieg et al. |
| 6,271,209 B1 | 8/2001 | Smith et al. |
| 6,406,705 B1 | 6/2002 | Davis et al. |
| 6,677,153 B2 | 1/2004 | Iversen |
| 7,223,833 B1 | 5/2007 | Nielsen et al. |
| 7,238,472 B2 | 7/2007 | Mirkin et al. |
| 7,667,004 B2 | 2/2010 | Zhong et al. |
| 7,833,992 B2 | 11/2010 | Vargeese et al. |
| 8,252,756 B2 | 8/2012 | Rosi et al. |
| 8,461,117 B2 | 6/2013 | Sufi et al. |
| 8,507,200 B2 | 8/2013 | Mirkin et al. |
| 8,664,407 B2 | 3/2014 | Chen et al. |
| 8,846,080 B2 | 9/2014 | Biemans et al. |
| 8,933,046 B2 | 1/2015 | Machuy et al. |
| 8,940,310 B2 | 1/2015 | Barrat et al. |
| 8,999,947 B2 | 4/2015 | Mirkin et al. |
| 9,376,690 B2 | 6/2016 | Mirkin et al. |
| 9,506,056 B2 | 11/2016 | Mirkin et al. |
| 9,693,957 B2 | 7/2017 | Lin et al. |
| 9,719,089 B2 | 8/2017 | Mirkin et al. |
| 9,757,475 B2 | 9/2017 | Mirkin et al. |
| 9,868,955 B2 | 1/2018 | Giducci et al. |
| 9,890,427 B2 | 2/2018 | Mirkin et al. |
| 9,901,616 B2 | 2/2018 | Dhar et al. |
| 10,182,988 B2 | 1/2019 | Mirkin et al. |
| 10,208,310 B2 | 2/2019 | Mader et al. |
| 10,301,622 B2 | 5/2019 | Mirkin et al. |
| 10,370,656 B2 | 8/2019 | Mirkin et al. |
| 10,792,251 B2 | 10/2020 | Mirkin et al. |
| 2002/0172711 A1 | 11/2002 | Martin et al. |
| 2003/0026782 A1 | 2/2003 | Krieg |
| 2003/0044354 A1 | 3/2003 | Carpenter et al. |
| 2003/0147966 A1 | 8/2003 | Franzen et al. |
| 2003/0170162 A1 | 9/2003 | Nayfeh et al. |
| 2004/0014956 A1 | 1/2004 | Woolf et al. |
| 2004/0033197 A1 | 2/2004 | Madar et al. |
| 2004/0053384 A1 | 3/2004 | Sligar et al. |
| 2004/0158051 A1 | 8/2004 | Ozkan et al. |
| 2004/0170560 A1 | 9/2004 | Fossheim et al. |
| 2004/0219565 A1 | 11/2004 | Kauppinen et al. |
| 2005/0130167 A1 | 6/2005 | Bao et al. |
| 2005/0232866 A1 | 10/2005 | Melchior et al. |
| 2006/0014191 A1 | 1/2006 | Lao et al. |
| 2006/0083781 A1 | 4/2006 | Shastri et al. |
| 2006/0292174 A1 | 12/2006 | de los Rios et al. |
| 2007/0243136 A1 | 10/2007 | Fisher et al. |
| 2007/0298257 A1 | 12/2007 | Ludwig et al. |
| 2008/0175893 A1 | 7/2008 | Huang et al. |
| 2008/0181928 A1 | 7/2008 | Hakimi-Mehr et al. |
| 2008/0194463 A1 | 8/2008 | Weller et al. |
| 2008/0311182 A1 | 12/2008 | Ferrari et al. |
| 2009/0018028 A1 | 1/2009 | Lindsay et al. |
| 2009/0053169 A1 | 2/2009 | Castillo et al. |
| 2009/0209629 A1 | 8/2009 | Mirkin et al. |
| 2009/0246142 A1 | 10/2009 | Bhatia et al. |
| 2009/0322327 A1 | 12/2009 | Gao |
| 2010/0003317 A1 | 1/2010 | Akinc et al. |
| 2010/0092486 A1 | 4/2010 | Kandimalla et al. |
| 2010/0144848 A1 | 6/2010 | Vogel et al. |
| 2010/0166842 A1 | 7/2010 | Lu et al. |
| 2010/0203149 A1 | 8/2010 | Radosz et al. |
| 2010/0233270 A1 | 9/2010 | Mirkin et al. |
| 2011/0020242 A1 | 1/2011 | Zheng et al. |
| 2011/0052680 A1 | 3/2011 | Hendrickson et al. |
| 2011/0052697 A1 | 3/2011 | Farokhzad et al. |
| 2011/0159081 A1 | 6/2011 | Biemans et al. |
| 2011/0223257 A1 | 9/2011 | Zhao et al. |
| 2011/0229529 A1 | 9/2011 | Irvine et al. |
| 2011/0237435 A1 | 9/2011 | Ryan |
| 2012/0149843 A1 | 6/2012 | Chien et al. |
| 2012/0282186 A1 | 11/2012 | Mirkin et al. |
| 2012/0283316 A1 | 11/2012 | Mirkin et al. |
| 2013/0028857 A1 | 1/2013 | Gao et al. |
| 2013/0089614 A1 | 4/2013 | Zhang et al. |
| 2013/0123333 A1 | 5/2013 | Mirkin et al. |
| 2013/0149374 A1 | 6/2013 | Lee et al. |
| 2013/0196951 A1 | 8/2013 | Schoenfisch et al. |
| 2013/0252852 A1 | 9/2013 | Pfeiffer et al. |
| 2013/0295129 A1 | 11/2013 | Irvine et al. |
| 2013/0309172 A1 | 11/2013 | Suresh et al. |
| 2013/0315831 A1 | 11/2013 | Shi et al. |
| 2014/0065425 A1 | 3/2014 | Bogdanov |
| 2015/0031745 A1 | 1/2015 | Mirkin et al. |

(56) References Cited

U.S. PATENT DOCUMENTS

| | | |
|---|---|---|
| 2015/0111790 A1 | 4/2015 | Ategeka et al. |
| 2016/0108123 A1 | 4/2016 | Freeman et al. |
| 2016/0186178 A1 | 6/2016 | Radovic-Moreno et al. |
| 2016/0194642 A1 | 7/2016 | Gryaznov et al. |
| 2016/0237429 A1 | 8/2016 | Cubillos-Ruiz et al. |
| 2016/0274134 A1 | 9/2016 | Mutharasan et al. |
| 2016/0310425 A1 | 10/2016 | Mirkin et al. |
| 2017/0157048 A1 | 6/2017 | Radovic-Moreno et al. |
| 2018/0072810 A1 | 3/2018 | Afar et al. |
| 2018/0222982 A1 | 8/2018 | Dranoff et al. |
| 2020/0022913 A1 | 1/2020 | Mirkin et al. |
| 2021/0122778 A1 | 4/2021 | Mirkin et al. |
| 2021/0123057 A1 | 4/2021 | Mirkin et al. |
| 2021/0220454 A1 | 7/2021 | Mirkin et al. |

FOREIGN PATENT DOCUMENTS

| | | |
|---|---|---|
| CN | 103212089 A | 7/2013 |
| EP | 1072679 A2 | 1/2001 |
| EP | 2162117 A2 | 3/2010 |
| EP | 2399608 A1 | 12/2011 |
| HK | 1152529 | 3/2012 |
| WO | 1996/34876 A1 | 11/1996 |
| WO | 1997/12896 A1 | 4/1997 |
| WO | 1998/39352 A1 | 9/1998 |
| WO | 1999/14226 A2 | 3/1999 |
| WO | 2002/96262 A2 | 12/2002 |
| WO | 2003/86280 A2 | 10/2003 |
| WO | 2005/063201 A2 | 7/2005 |
| WO | 2005/063288 A1 | 7/2005 |
| WO | 2006/138145 A1 | 12/2006 |
| WO | 2007/008463 A2 | 1/2007 |
| WO | 2007/064857 A2 | 6/2007 |
| WO | 2007/096134 A1 | 8/2007 |
| WO | 2008/014979 A2 | 2/2008 |
| WO | 2008/151022 A2 | 12/2008 |
| WO | 2008/151049 A2 | 12/2008 |
| WO | 2009/061515 A1 | 5/2009 |
| WO | 2009/073984 A1 | 6/2009 |
| WO | 2009/120887 A2 | 10/2009 |
| WO | 2010/060110 A1 | 5/2010 |
| WO | 2010/105209 A1 | 9/2010 |
| WO | 2010/120420 A1 | 10/2010 |
| WO | 2011/017456 A2 | 2/2011 |
| WO | 2011/028850 A1 | 3/2011 |
| WO | 2012/055933 A1 | 5/2012 |
| WO | 2012/068470 A2 | 5/2012 |
| WO | 2013/012628 A2 | 1/2013 |
| WO | 2013/028843 A1 | 2/2013 |
| WO | 2013/049941 A1 | 4/2013 |
| WO | 2013/151771 A1 | 10/2013 |
| WO | 2014/169264 A2 | 10/2014 |
| WO | 2015/013673 A1 | 1/2015 |
| WO | 2015/013675 A1 | 1/2015 |
| WO | 2015/126502 A2 | 8/2015 |
| WO | 2015/187966 A1 | 12/2015 |
| WO | 2016/028940 A1 | 2/2016 |
| WO | 2016/081911 A2 | 5/2016 |
| WO | WO 2016/149323 A1 * | 9/2016 |
| WO | 2017/031086 A1 | 2/2017 |
| WO | 2017/035278 A1 | 3/2017 |
| WO | 2018/067302 A2 | 4/2018 |
| WO | 2018/152327 A1 | 8/2018 |
| WO | 2018/175445 A1 | 9/2018 |
| WO | 2018/213585 A1 | 11/2018 |
| WO | 2019/032241 A1 | 2/2019 |
| WO | 2019/070890 A1 | 4/2019 |
| WO | 2019/118883 A1 | 6/2019 |
| WO | 2019/200262 A1 | 10/2019 |
| WO | 2019/217870 A1 | 11/2019 |
| WO | 2020/056341 A2 | 3/2020 |
| WO | 2020/068905 A1 | 4/2020 |
| WO | 2020/118259 A1 | 6/2020 |
| WO | 2020/181144 A1 | 9/2020 |
| WO | 2020/257674 A1 | 12/2020 |
| WO | 2021/034956 A2 | 2/2021 |
| WO | 2021/177996 A1 | 9/2021 |
| WO | 2021/207630 A1 | 10/2021 |

OTHER PUBLICATIONS

Zhang et al., Structure-activity relationships of cationic shell-crosslinked knedel-like nanoparticles: shell composition and transfection efficiency/cytotoxicity, Biomaterials, 31:1805-1813 (2010).

Zheng et al., A spherical nucleic acid platform based on self-assembled DNA biopolymer for high-performance cancer therapy, ACS Nano, 7(8):6545-6554 (2013).

Zheng et al., Aptamer nano-flares for molecular detection in living cells, Nano Lett., 9(9):3258-3261 (2009).

Zhu et al., Matrix metalloprotease 2-responsive multifunctional liposomal nanocarrier for enhanced tumor targeting, ACS Nano., 6(4):3491-3498 (2012).

Zimmermann et al., A novel silver(i)-mediated DNA base pair, J. Am. Chem. Soc., 124(46):13684-13685 (2002).

Fattal et al., Biodegradable polyalkylcyanoacrylate nanoparticles for the delivery of oligonucleotides, J. Controlled Release, 53(1-3):137-143 (1998).

Ferrari, Cancer nanotechnology: opportunities and challenges, Nature Reviews Cancer, 5:161-171 (2005).

Freier et al., The ups and downs of nucleic acid duplex stability: structure-stability studies on chemically-modified DNA:RNA duplexes, Nucl. Acid. Res., 25:4429-4443 (1997).

Frens, Controlled Nucleation for the Regulation of the Particle Size in Monodisperse Gold Suspensions, Nature Physical Science, 241:20-22 (1973).

Furumoto et al., Effect of coupling of albumin onto surface of PEG liposome on its in vivo disposition, International Journal of Pharmaceutics, 329(1-2):110-116 (2007).

Garcia-Alvarez et al., Kostarelos, K., In vivo formation of protein corona on gold nanoparticles. The effect of their size and shape, Nanoscale, 10(3):1256-1264 (2018).

Giljohann et al., Gene regulation with polyvalent siRNA-nanoparticle conjugates, J. Am. Chem. Soc., 131(6):2072-2073 (2009).

Giljohann et al., Gold nanoparticles for biology and medicine, Angew. Chem. Int. Ed. Engl., 49(19):3280-3294 (2010).

Giljohann et al., Oligonucleotide loading determines cellular uptake of DNA-modified gold nanoparticles, Nano Letters, 7(12):3818-3821 (2007).

Grijalva et al., Oligonucleotide delivery: a patent review (2010-2013), Expert Opin. Ther. Pat., 24(7):801-819 (2014).

Gunnarsson et al., Liposome-based chemical barcodes for single molecule DNA detection using imaging mass soectrometry, Nano. Lett., 10:732-737 (2010).

Gunnarsson et al., Single-molecule detection and mismatch discrimination of unlabeled DNA targets, Nano Lett., 8:183-188 (2008).

Hatakeyama et al., Development of a novel systemic gene delivery system for cancer therapy with a tumor-specific cleavable PEG-lipid, Gene Ther., 14(1)68-77 (2006).

Hayashi, Ultrafine Particles, Physics Today, 44-60 (1987).

Hayashi, Ultrafine Particles, Vac. Sci. Technol., A5(4):1375-84 (1987).

He et al., Catalytic Molecular Imaging of MicroRNA in Living Cells by DNA-Programmed Nanoparticle Disassembly, Angewandte Chemie International Edition, 55(9):3073-3076 (2016).

Henglein et al., Absorption spectrum and some chemical reactions of colloidal platinum in aqueous solution, J. Phys. Chem., 99(38):14129-14136 (1995).

Henglein, Mechanism of reactions on colloidal microelectrodes and size quantization effects, Top. Curr. Chem., 143:113-180 (1988).

Henglein, Small-particle research: physicochemical properties of extremely small colloidal metal and semiconductor particles, Chem. Rev., 89(8):1861-1873 (1989).

Hope et al., Generation of multilamellar and unilamellar phospholipid vesicles, Chemistry and Physics of Lipids, 40:89-107(1986).

(56) References Cited

OTHER PUBLICATIONS

Hope et al., Production of large unilamellar vesicles by a rapid extrusion procedure: characterization of size distribution, trapped volume and ability to maintain a membrane potential, Biochim Biophys Acta, 812:55-65 (1985).

Houot et al., T-cell modulation combined with intratumoral CpG cures lymphoma in a mouse model without the need for chemotherapy, Blood, 113(15):3546-3552 (2009).

Hurst et al., Maximizing DNA loading on a range of gold nanoparticle sizes, Anal. Chem., 78(24):8313-8318 (2006).

International Application No. PCT/US2018/054221, International Preliminary Report on Patentability, mailed Apr. 16, 2020.

International Application No. PCT/US2018/054221, International Search Report and Written Opinion, mailed Dec. 26, 2018.

International Preliminary Report on Patentability, United States Patent Office, PCT/US2014/068429, dated Jun. 7, 2016.

International Search Report and Written Opinion of the International Search Authority, United States Patent Office, PCT/US2014/068429, dated Aug. 10, 2015.

Jahn et al., Microfluidic directed formation of liposomes of controlled size, Langmuir, 23(11):6289-6293 (2007).

Jakobsen et al., Assembly of liposomes controlled by triple helix formation, Bioconjugate Chem., 24:1485-1495 (2013).

Jensen et al., Spherical nucleic acid nanoparticle conjugates as an RNAi-based therapy for glioblastoma, Sci. Transl. Med., 5(209):209ra152-209ra152 (2013).

Jiang et al., Quantitative analysis of the protein corona on FePt nanoparticles formed by transferrin binding, Journal of the Royal Society, Interface, 7(Suppl 1):S5-S13 (2010).

Jiang et al., Tumor imaging by means of proteolytic activation of cell-penetrating peptides, Proc. Natl. Acad. Sci. U.S.A., 101(51):17867-17872 (2004).

Kandimalla et al., Secondary structures in CpG oligonucleotides affect immunostimulatory activity, Biochemical and Biophysical Research Communications, 306:948-953 (2003).

Kasuya et al., Bio-nanocapsule-liposome conjugates for in vivo pinpoint drug and gene delivery, Methods Enzymol., 464:147-166 (2009).

Katz, The reversible reaction of sodium thymonucleate and mercuric chloride, J. Am. Chem. Soc., 74(9):2238-2245 (1951).

Kelly et al., Targeted liposomal drug delivery to monocytes and macrophages, Journal of Drug Delivery, Article ID 727241:1-11 (2011).

Kelty et al., High-throughput synthesis and characterization of nanocrystalline porphyrinic zirconium metal-organic frameworks, Chem. Commun(Camb), 52(50):7854-7857 (2016).

Kim et al., Cationic solid lipid nanoparticles reconstituted from low density lipoprotein components for delivery of siRNA, Mol. Pharm., 5(4):622-631 (2008).

Kim et al., Effect of bovine serum albumin on the stability of methotrexate-encapsulated liposomes, Arch. Pharmacal Res., 14:336-341 (1991).

Kosturko et al., The crystal and molecular structure of a 2:1 complex of 1-methylthymine-mercury (II), Biochemistry, 13(19):3949-3952 (1974).

Kreig, Toll-like receptor 9 (TLR9) agonists in the treatment of cancer, Oncogene, 27:116-167 (2008).

Kroschwitz et al., The concise encyclopedia of polymer science and engineering, John Wiley & Sons, 858-859 (1990).

Kukowska-Latallo et al., Efficient transfer of genetic material into mammalian cells using Starburst polyamidoamine dendrimers, Proc. Natl. Acad. Sci. USA, 93(10):4897-4902 (1996).

Kulkarni et al., Mmp-9 responsive PEG cleavable nanovesicles for efficient delivery of chemotherapeutics to pancreatic cancer, Molecular Pharmaceutics, 11(7):2390-2399 (2014).

Labib et al., Single-cell mRNA cytometry via sequence-specific nanoparticle clustering and trapping, Nature Chemistry, 10:489-495 (2018).

Laouini et al., Preparation, characterization and applications of liposomes: state of the art, Journal of Colloid Science and Biotechnology, 1:148-168 (2012).

Lee et al., Imageable Antigen-Presenting Gold Nanoparticle Vaccines for Effective Cancer Immunotherapy In vivo, Angewandte Chemie International Edition, 51(35):8800-8805 (2012).

Lee et al., Silver nanoparticle-oligonucleotide conjugates based on DNA with triple cyclic disulfide moieties, Nano Lett., 7(7):2112-2115 (2007).

Lesieur et al., Size analysis and stability study of lipid vesicles by high-performance gel exclusion chromatography, turbidity, and dynamic light scattering, Analytical Biochemistry, 192(2):334-343 (1991).

Li et al., Combination Delivery of Antigens and CpG by Lanthanides-Based Core-Shell Nanoparticles for Enhanced Immune Response and Dual-Mode Imaging, Advanced Healthcare Materials, 2(10):1309-1313 (2013).

Li et al., Molecular spherical nucleic acids, PNAS, 115(17):4340-4344 (2018).

Li et al., Nucleolin-targeting liposomes guided by aptamer AS1411 for the delivery of siRNA for the treatment of malignant melanomas, Biomaterials, 35(12):3840-3850 (2014).

Li et al., Reversible and Chemically Programmable Micelle Assembly with DNA Block-Copolymer Amphiphiles, Nano Lett., 4(6):1055-1058 (2004).

Li et al., Smart asymmetric vesicles with triggered availability of inner cell-penetrating shells for specific intracellular drug delivery, ACS Appl. Mater. Interfaces, 9(21):17727-17735 (2017).

Li et al., Synthesis of nanocrystals of Zr-based metal-organic frameworks with csq-net: significant enhancement in the degradation of a nerve agent simulant, Chem. Commun., 51(54):10925-10928 (2015).

Li et al., Thermal stability of DNA functionalized gold nanoparticles, Bioconjugate Chem., 24:1790-1797 (2013).

Lin et al., Gold Nanoparticle Delivery of Modified CpG Stimulates Macrophases and Inhibits Tumor Growth for Enhanced Immunotherapy, PLoS One, 8(5):e63550 (2013).

Liu et al., DNA-based micelles: synthesis, micellar properties and size-dependent cell permeability, Chemistry, 16:3791-3797 (2010).

Liu et al., Freezing directed construction of Bio/Nano interfaces: reagentless conjugation, Denser spherical nucleic acids, and better nanoflares, J. Am. Chem. Soc., 139(28): 9471-9474 (2017).

Liu et al., Membrane anchored immunostimulatory oligonucleotides for in vivo cell modification and localized immunotherapy, Angew. Chem. Int. Ed. Engl., 50(31):7052-7055 (2011).

Liu et al., New poly(d-glucaramidoamine)s induce DNA nanoparticle formation and efficient gene delivery into mammalian cells, J. Am. Chem. Soc., 126(24):7422-7423 (2004).

Liu et al., Silica nanoparticle supported lipid bilayers for gene delivery, Chem. Commun., 5100-5102 (2009).

Liu et al., Surface and Size Effects on Cell Interaction of Gold Nanoparticles with Both Phagocytic and Nonphagocytic Cells, Langmuir, 29(29):9138-9148 (2013).

Lundqvist et al., Nanoparticle size and surface properties determine the protein corona with possible implications for biological impacts, Proc. Natl. Acad. Sci. USA, 105(38):14265-70 (2008).

Luo et al., MicroRNA-Catalyzed Cancer Therapeutics Based on DNA-Programmed Nanoparticle Complex, ACS Appl Mater Interfaces, 9(39):33624-33631 (2017).

Lytton-Jean et al., Highly Cooperative Behavior of Peptide Nucleic Acid Linked DNA Modified Gold Nanoparticle and Combo Polymer Aggregates, Advanced Materials, 21(6):706-709 (2009).

Mangsbo et al., Enhanced Tumor Eradication by Combining CTLA-4 or PD-1 Blockage with CpG Therapy, Journal of Immunotherapy, 33(3)1225-235 (2010).

Manson et al., Polyethylene glycol functionalized gold nanoparticles: the influence of capping density on stability in various media, Gold Bulletin, 44(2):99-105 (2011).

Marinakos et al., Gold nanoparticles as templates for the synthesis of hollow nanometer-sized conductive polymer capsules, Adv. Mater., 11(1):34-37 (1999).

(56) References Cited

OTHER PUBLICATIONS

Marinakos et al., Template synthesis of one-dimensional Au, Au-poly(pyrrole), and poly(pyrrole) nanoparticle arrays, Chem. Mater., 10(5):1214-19 (1998).
Martin et al., Ein neur Zugang zu 2'-O-alkylribonucleosiden and Eigenschaften deren oligonucleotide, Hely. Chim. Acta., 78:486-504 (1995).
Massart, Preparation of aqueous magnetic liquids in alkaline and acidic media, IEEE Transactions On Magnetics, 17(2):1247-1248 (1981).
Massich et al., Regulating Immune Response Using Polyvalent Nucleic Acid-Gold Nanoparticle Conjugates, Molecular Pharmaceutics, 6(6):1934-1940 (2009).
Matijevic et al., Fine Particles Part II: Formation Mechanisms and Applications, MRS Bulletin, 16-47 (1990).
McAllister et al., Polymeric nanogels produced via inverse microemulsion polymerization as potential gene and antisense delivery agents, J. Am. Chem. Soc., 124:15198-15207 (2002).
Mesmaeker et al., Backbone modifications in oligonucleotides and peptide nucleic acid systems, Curr. Opin. In Struct. Biol., 5:343-355 (1995).
Mirkin et al., A DNA-based method for rationally assembling nanoparticles into macroscopic materials, Nature, 382(6592):607-609 (1996).
Mirshafiee et al., Impact of protein pre-coating on the protein corona composition and nanoparticle cellular uptake, Biomaterials, 75:295-304 (2016).
Mirshafiee et al., Protein corona significantly reduces active targeting yield, Chemical Communications, 49(25):2557-2559 (2013).
Mohamed et al., Effect of toll-like receptor 7 and 9 targeted therapy to prevent the development of hepatocellular carcinoma, Liver Int., 35(3):1063-1076 (2015).
Mohamed et al., TLR9 mediates *S. aureus* killing inside osteoblasts via induction of oxidative stress, BMC Microbiology, 16(article 230):8 (2016).
Molina et al., Trastuzumab (Herceptin), a Humanized Anti-HER2 Receptor Monoclonal Antibody, Inhibits Basal and Activated HER2 Ectodomain Cleavage in Breast Cancer Cells, Cancer Research, 61(12):4744-4749 (2001).
Molino et al., Display of DNA on Nanoparticles for Targeting Antigen Presenting Cells, ACS Biomaterials Science & Engineering, 3(4):496-501 (2017).
Nagase, Substrate specificity of MMPs. In matrix metalloproteinase inhibitors in cancer therapy, Springer: 39-66 (2001).
Nguyen et al., Enzyme-responsive nanoparticles for targeted accumulation and prolonged retention in heart tissue after myocardial infarction, Advanced Materials, 27(37):5547-5552 (2015).
Nguyen et al., Protein corona: a new approach for nanomedicine design, International Journal of Nanomedicine, 12:3137-3151 (2017).
Nielsen et al., Sequence-selective recognition of DNA by strand displacement with a thymine-substituted polyamide, Science, 254:1497-500 (1991).
Nikolov et al., Bias-dependent admittance in hybrid bilayer membranes, Langmuir, 22(17):7156-7158 (2006).
Ogawara et al., Pre-coating with serum albumin reduces receptor-mediated hepatic disposition of polystyrene nanosphere: implications for rational design of nanoparticles, Journal of Controlled Release, 100(3):451-455 (2004).
Olshavsky et al., Organometallic synthesis of gallium-arsenide crystallites, exhibiting quantum confinement, J. Am. Chem. Soc., 112(25):9438-9439 (1990).
Olson et al., Activatable cell penetrating peptides linked to nanoparticles as dual probes for in vivo fluorescence and MR imaging of proteases, Proceedings of the National Academy of Sciences, 107(9):4311-4316 (2010).
Otsuka et al., PEGylated nanoparticles for biological and pharmaceutical applications, Adv. Drug Delivery. Rev., 64:246-255 (2012).
Ozpolat et al., Nanomedicine based approaches for the delivery of siRNA in cancer, J. Intern. Med., 267(1):44-53 (2010).
Patel et al., Scavenger receptors mediate cellular uptake of polyvalent oligonucleotide-functionalized gold nanoparticles, Bioconjugate Chem., 21(12):2250-2256 (2010).
Peter et al., Characterization of suppressive oligodeoxynucleotides that inhibit Toll-like receptor-9-mediated activation of innate immunity, Immunology, 123(1):118-128 (2008).
Pfeiffer et al., Bivalent Cholesterol-Based Coupling of Oligonucleotides to Lipid Membrane Assemblies, J. Am. Chem. Soc., 126:10224-10225 (2004).
Pfeiffer et al., Quantification of oligonucleotide modifications of small unilamellar lipid vesicles, Anal. Chem., 78:7493-7498 (2006).
Potter et al., The opsonization of bentonite particles by gammaglobulin, Journal of Immunology, 87:110-118 (1961).
Prigodich et al., Nano-flares for mRNA Regulation and Detection, ACS Nano, 3(8):2147-2152 (2009).
Prozeller et al., Prevention of Dominant IgG Adsorption on N anocarriers in IgG-Enriched Blood Plasma by Clusterin Precoating, Advanced Science, 6(10):1802199 (2019).
Radovic-Moreno et al., Immunomodulatory spherical nucleic acids, Proc. Natl. Acad. Sci. U.S.A., 112(13):3892-3897 (2015).
Ritz et al., Protein Corona of Nanoparticles: Distinct Proteins Regulate the Cellular Uptake, Biomacromolecules, 16(4):1311-1321 (2015).
Rosi et al., Nanostructures in biodiagnostics, Chem. Rev., 105(4):1547-1562 (2005).
Rosi et al., Oligonucleotide-modified gold nanoparticles for intracellular gene regulation, Science, 312(5776):1027-1030 (2006).
Rostovtsev et al., A stepwise huisgen cycloaddition process: copper(I)-catalyzed regioselective "Ligation" of azides and terminal alkynest, Angewandte Chemie, 114(14): 2708-2711 (2002).
Ruan et al., DNA nanoclew templated spherical nucleic acids for siRNA delivery, Chemical Communications, 54(29):3609-3612 (2018).
Saha et al., Regulation of Macrophage Recognition through the Interplay of Nanoparticle Surface Functionality and Protein Corona, ACS Nano, 10(4):4421-30 (2016).
Salvati et al., Transferrin-functionalized nanoparticles lose their targeting capabilities when a biomolecule corona adsorbs on the surface, Nat. Nanotechnol., 8:137-143 (2013).
Sanghvi, Chapter 15, Antisense research and applications, Crooke, S. T. and Lebleu, B., ed., CRC Press, 289-302 (1993).
Schaffler et al., Blood protein coating of gold nanoparticles as potential tool for organ targeting, Biomaterials, 35(10):3455-66 (2014).
Schottler et al., Protein adsorption is required for stealth effect of poly(ethylene glycol)- and poly(phosphoester)-coated nanocarriers, Nat. Nanotechnol., 11:372-377 (2016).
Seferos et al., Locked nucleic acid-nanoparticle conjugates, ChemBioChem, 8:1230-1232 (2007).
Seferos et al., Nano-flares: probes for transfection and mRNA detection in living cells, J. Am. Chem. Soc., 129(50):15477-15479 (2007).
Seferos et al., Polyvalent DNA nanoparticle conjugates stabilize nucleic acids, Nano Lett., 9(1 ):308-311 (2009).
Senior et al., Stability of small unilamellar liposomes in serum and clearance from the circulation: the effect of the phospholipid and cholesterol components, Life Sci., 30:2123-2136 (1982).
Simon et al., Exploiting the biomolecular corona: pre-coating of nanoparticles enables controlled cellular interactions, Nanoscale, 10(22):10731-10739 (2018).
Slack et al., Rotaxane probes for protease detection by 129 Xe hyperCEST NMR, Chemical Communications, 53(6):1076-1079 (2017).
Small et al., Facilitating THP-1 macrophage studies by differentiating and investigating cell functions in polystyrene test tubes, Journal of Immunological Methods, 461:73-77 (2018).
Sobota et al., Binding of IgG-opsonized particles to FcyR is an active stage of phagocytosis that involves receptor clustering and phosphorylation, Journal of Immunology, 175(7):4450-4457 (2005).
Sokolova et al., The use of calcium phosphate nanoparticles encapsulating Toll-like receptor ligands and the antigen hemagglutinin to induce dendritic cell maturation and T cell activation, Biomaterials, 31:5627-5633 (2010).

(56) References Cited

OTHER PUBLICATIONS

Sprangers et al., Liposomal spherical nucleic acids for regulating long noncoding RNAs in the nucleus, Small, 13(10):10.1002/smll.201602753 (2016).
Staufenbiel et al., Targeting of Intravenous Polymeric Nanoparticles by Differential Protein Adsorption, Macromolecular Symposia, 345(1):42-50 (2014).
Stengel et al., Determinants for Membrane Fusion Induced by Cholesterol-Modified DNA Zippers, J. Phys. Chem. B., 112:8264-74 (2008).
Stengel et al., DNA-Induced Programmable Fusion of Phospholipid Vesicles, J. Am. Chem. Soc., 129:9584-5 (2007).
Sulkowski et al., The influence of temperature, cholesterol content and pH on liposome stability, J. Mol. Struct., 744-747:737-747 (2005).
Switaj et al., CpG Immunostimulatory Oligodeoxynucleotide 1826 Enhances Antitumor Effect of Interleukin 12 Gene-Modified Tumor Vaccine in a Melanoma Model in Mice, Clinical Cancer Research, 10:4165-4175 (2004).
Thomas, The Interaction of HgCl2 with sodium thymonucleate, J. Am. Chem. Soc., 76(23):6032-6034 (1954).
Tincer et al., Immunostimulatory activity of polysccharidepoly (I:C) nanoparticles, Biomaterial., 32(18):4275-4282 (2011).
Tondelli et al., Highly efficient cellular uptake of c-myb antisense oligonucleotides through specifically designed polymeric nanospheres, Nucl. Acids Res., 26(23):5425-5431 (1998).
Tonigold et al., Pre-adsorption of antibodies enables targeting of nanocarriers despite a biomolecular corona, Nat. Nanotechnol., 13(9):862-869 (2018).
Uchida et al., Gallium arsenide nanocrystals prepared in quinoline, J. Phys. Chem., 95:5382 (1992).
Veiseh et al., Optical and MRI multifunctional nanoprobe for targeting gliomas, Nano Lett., 5(6):1003-1008 (2005).
Versluis et al., In situ modification of plain liposomes with lipidated coiled coil forming peptides induces membrane fusion, J. Am. Chem. Soc., 135:8057-8062 (2013).
Wang et al., Altering DNA-Programmable Colloidal Crystallization Paths by Modulating Particle Repulsion, Nano Letters, 17:5126-32 (2017).
Wang et al., Nanometer-sized semiconductor clusters: materials synthesis, quantum size effects, and photophysical properties, J. Phys. Chem., 95:525-532 (1991).
Wang et al., Rational vaccinology with spherical nucleic acids, Proceedings of the National Academy of Sciences, 116(21):10473-10481 (2019).
Wei et al., Polyvalent Immunostimulatory Nanoagents with Self-Assembled CpG Oligonucleotide-Conjugated Gold Nanoparticles, Angewandte Chemie International Edition, 51(5):1202-1206 (2012).
Weller, Colloidal semiconductor Q-particles: Chemistry in the transition region between solid state and molecules, Angew. Chem. Int. Ed. Engl., 32(1):41-53 (1993).
West et al., Recognition and signaling by toll-like receptors, Annu. Rev. Cell Dev. Biol., 22:409-37 (2006).
Whitehead et al., Knocking down barriers: advances in siRNA delivery, Nat. Rev. Drug. Discov., 8:129-138 (2009).
Willis et al., Liposome-Anchored Vascular Endothelial Growth Factor Aptamers, Bioconjugate Chem., 9 573-582 (1998).
Wilson et al., pH-Responsive Nanoparticle Vaccines for Dual-Delivery of Antigens and Immunostimulatory Oligonucleotides, ACS NANO, 7(5):3912-3925 (2013).
Wu et al., DNA aptamer-micelle as an efficient detection/delivery vehicle toward cancer cells, Proc. Natl. Acad. Sci. SA., 107(1):5-10 (2010).
Xing et al., Selective delivery of an anticancer drug with aptamer-functionalized liposomes to breast cancer cells in vitro and in vivo, J. Mater. Chem. B., 1:5288-5297 (2013).
Yamane et al., On the complexing of desoxyribonucleic acid (DNA) by mercuric ion1, J. Am. Chem. Soc., 83(12):2599-2607 (1961).

Yan et al., Differential roles of the protein corona in the cellular uptake of nanoporous polymer particles by monocyte and macrophage cell lines, ACS Nano, 7(12):10960-70 (2013).
Yang et al., FRET Nanoflares for Intracellular mRNA Detection: Avoiding False Positive Signals and Minimizing Effects of System Fluctuations, Journal of the American Chemical Society, 137(26):8340-8343 (2015).
Yin et al., Supramolecular self-assembled nanoparticles mediate oral delivery of therapeutic TNF-? siRNA against systemic inflammation, Anaew. Chem. Int. Ed. Enal., 125(22):5757-5761 (2013).
Young et al., Hollow spherical nucleic acids for intracellular gene regulation based upon biocompatible silica shells, Nano Lett., 12(7):3867-3871 (2012).
Zhang et al., A general approach to DNA-programmable atom equivalents, Nat. Mater., 12(8)741-746 (2013).
Agbasi-Porter et al., Transcription inhibition using oligonucleotide-modified gold nanoparticles, Bioconiugate Chem., 17(5):1178-83 (2006).
Aguilera et al., Systemic in vivo distribution of activatable cell penetrating peptides is superior to that of cell penetrating peptides, Integrative Biology, 1(5-6):371-381 (2009).
Ahmadi et al., Shape-controlled synthesis of colloidal platinum nanoparticles, Science, 272(5270):1924-6 (1996).
Ahmed et al., Human serum albumin-based probes for molecular targeting of macrophage scavenger receptors, International Journal of Nanomedicine, 14:3723-3741 (2019).
Alemdaroglu et al., DNA block copolymer micelles—A combinatorial tool for cancer tanotechnology, Advanced Materials, 20:899 (2008).
Ali et al., Vaccines combined with immune checkpoint antibodies promote cytotoxic T-cell activity and tumor eradication, Cancer Immunology Research, 4(2):95-100 (2016).
Altschul et al., Basic local alignment search tool, J. Mol. Biol., 215(3):403-410 (1990).
Andrews et al., Conjugation of lipid and CpG-containing oligonucleotide yields an efficient method for liposome incorporation, Bioconjugate Chem., 22:1279-1286 (2011).
Aoyama et al., Clusterin in the protein corona plays a key role in the stealth effect of nanoparticles against phagocytes, Biochem Biophys Res. Commun., 480(4):690-695 (2016).
Bae et al., Targeted drug delivery to tumors: myths, reality and possibility, J. Control Release, 153(3)1198-205 (2011).
Bahnemann, in Photochemical conversion and storage of solar energy (eds. Pelizetti and Schiavello, 251 (1991).
Banchelli et al., Phospholipid membranes decorated by cholesterol-based oligonucleotides as soft hybrid nanostructures, J. Phys. Chem. B., 112:10942-10952 (2008).
Banga et al., Cross-linked micellar spherical nucleic acids from thermoresponsive templates, J. Am. Chem. Soc., (2017).
Banga et al., Liposomal spherical nucleic acids, J. Am. Chem. Soc., 136(28):9866-9869 (2014).
Bouderault et al., Nanoscale tools to selectively destroy cancer cells, Chem. Commun., (18):2118-2120 (2008).
Briley et al., In Nanomaterials for Biomedicine; American Chemical Society, 1119:1-20 (2012).
Brodin et al., DNA-mediated cellular delivery of functional enzymes, J. Am. Chem. Soc., 137(47):14838-14841 (2015).
Brus, Quantum crystallites and nonlinear optics, Appl. Phys. A., 53:465-474 (1991).
Bunge et al., Lipophilic oligonucleotides spontaneously insert into lipid membranes, bind complementary DNA strands, and sequester into lipid-disordered domains, Langmuir, 23:4455-4464 (2007).
Burgess, Liposome preparation—Avanti(Registered) Polar Lipids, Sigma-Aldrich, 3 pages (1998).
Cagdas et al., Liposomes as potential drug carrier systems for drug delivery, In Application of Nanotechnology in Drug Delivery, Chapter 1, 51 pages (2014).
Cai et al., The Crown and the Scepter: Roles of the Protein Corona in Nanomedicine, Adv. Mater., 31(45):e1805740 (2019).
Calabrese et al., Biocompatible infinite-coordination-polymer nanoparticle-nucleic acid conjugates for antisense gene regulation, Angew. Chem. Int. Ed. Engl., 54(2):476-480 (2015).

(56) References Cited

OTHER PUBLICATIONS

Cao et al., Reversible cell-specific drug delivery with aptamer-functionalized liposomes, Angew. Chem. Int. Ed., 48:6494-6498 (2009).

Capaccioli et al., Cationic lipids improve antisense oligonucleotide uptake and prevent degradation in cultured cells and inhuman serum, Biochem. Biophys. Res. Commun., 197(2):818-825 (1993).

Cedervall et al., Understanding the nanoparticle-protein corona using methods to quantify exchange rates and affinities of proteins for nanoparticles, Proceedings of the National Academy of Sciences, 104(7):2050-2055 (2007).

Chien et al., DNA-nanoparticle micelles as supramolecular fluorogenic substrates enabling catalytic signal amplification and detection by DNAzyme probes, Chem. Commun., 47:167-169 (2011).

Chinen et al., Relationships between Poly(ethylene glycol) modifications on RNA-spherical nucleic acid conjugates and cellular uptake and circulation time, Bioconjugate Chemistry, 27(11):2715-2721 (2016).

Chinen et al., The Impact of Protein Corona Formation on the Macrophage Cellular Uptake and Biodistribution of Spherical Nucleic Acids, Small, 13(16):1603847 (2017).

Chinnathambi et al., Binding mode of CpG oligodeoxynucleotides to nanoparticles regulates bifurcated cytokine induction via Toll-like receptor 9, Scientific Reports, 2(534):1-9 (2012).

Cho et al., Targeted delivery of siRNA-generating DNA nanocassettes using multifunctional nanoparticles, Small, 9(11): 1964-1973 (2013).

Cho et al., Therapeutic nanoparticles for drug delivery in cancer, Clin. Cancer Res., 14(5)11310-1316 (2008).

Choi et al., Mechanism for the endocytosis of spherical nucleic acid nanoparticle conjugates, Proc. Natl. Acad. Sci. U.S.A., 110(19):7625-7630 (2013).

Concise encyclopedia of polymer science and engineering, J. I. Kroschwitz Ed., John Wiley & Sons, 858-859 (1990).

Cook, Medicinal chemistry of antisense oligonucleotides-future opportunities, Anti-Cancer Drug Design, 6(6):585-607 (1991).

Curtis et al., A morphology-selective copper organosolt, Angew. Chem. Int. Ed. Engl., 27(11):1530-1533 (1988).

Cutler et al., Polyvalent nucleic acid nanostructures, J. Am. Chem. Soc., 133(24)19254-9257 (2011).

Cutler et al., Polyvalent oligonucleotide iron oxide nanoparticle "click" conjugates, Nano Lett., 10(4)11477-1480 (2010).

Cutler et al., Spherical nucleic acids, J. Am. Chem. Soc., 134(3):1376-1391 (2012).

Dai et al., Monoclonal Antibody-Functionalized Multilayered Particles: Targeting Cancer Cells in the Presence of Protein Coronas, ACS Nano, 9(3):2876-2885 (2015).

Daigneault et al., The Identification of Markers of Macrophage Differentiation in PMA-Stimulated THP-1 Cells and Monocyte-Derived Macrophages, PLoS One, 5(1):e8668 (2010).

Dave et al., Programmable assembly of DNA-functionalized liposomes by DNA, ACS Nano, 5(2)11304-1312 (2011).

Docter et al., Quantitative profiling of the protein coronas that form around nanoparticles, Nature Protocols, 9:2030-2044 (2014).

Dua et al., Liposomei Methods of Preparation and Applications, International Journal of Pharmaceutical Studies and Research, 3(2)114-20 (2012).

Elbakry et al., Layer-by-layer assembled gold nanoparticles for siRNA delivery, Nano Lett., 9(5):2059-64 (2009).

Englisch et al., Chemically modified oligonucleotides as probes and inhibitors, Angew. Chem. Int. Ed., 30(6):613-629 (1991).

Enustun et al., Coagulation of colloidal gold, J. Am. Chem. Soc., 85(21):3317-3328 (1963).

European Application No. 14883485, European Search Report and Opinion, mailed May 9, 2017.

Fang et al., Functionalized nanoparticles with long-term stability in biological media, Small, 5(14):1637-1641 (2009).

Farokhzad et al., Nanomedicine: developing smarter therapeutic and diagnostic modalities, Drug Delivery Rev., 58(14):1456-1459 (2006).

\* cited by examiner

SPHERICAL NUCLEIC ACIDS WITH TAILORED AND ACTIVE PROTEIN CORONAE

CROSS-REFERENCE TO RELATED APPLICATIONS

This application claims the priority benefit under 35 U.S.C. § 119(e) of U.S. Provisional Patent Application No. 62/903,223, filed Sep. 20, 2019, which is incorporated herein by reference in its entirety.

STATEMENT OF GOVERNMENT INTEREST

This invention was made with government support under CA199091 and CA208783 awarded by the National Institutes of Health (NIH). The government has certain rights in the invention.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "2019-161_Seqlisting.txt", which was created on Sep. 17, 2020 and is 1,645 bytes in size. The subject matter of the Sequence Listing is incorporated herein in its entirety by reference.

FIELD

The disclosure is generally related to spherical nucleic acids (SNAs) comprising a protein corona, wherein the SNA comprises (i) a nanoparticle core and (ii) one or more oligonucleotides attached to the surface of the nanoparticle core, and wherein the protein corona comprises a plurality of proteins. The disclosure also provides methods of methods of using the same.

BACKGROUND

Certain nanomaterials can carry and present peptides, proteins, oligonucleotides, and small molecules within highly engineered structures to target tissues, making them appealing for biomedical and life science applications. However, many nanomaterials, when introduced to biological fluids, non-specifically adsorb biomolecules, resulting in the formation of a protein corona around the structure.[1] The protein corona alters the blood circulation time,[2-5] biodistribution,[6-7] and targeting efficiency[8-11] of the nanomaterials, sometimes diminishing their therapeutic potential. Though the surface charge,[12-13] size[6, 14-15] and shape[15] of the nanomaterial can modulate the composition of the protein corona, its formation is largely unavoidable in biological environments.

SUMMARY

Spherical nucleic acids (SNAs), a unique class of nanomaterials consisting of a spherical nanoparticle core densely functionalized with a highly oriented nucleic acid shell,[20-21] have enhanced biological properties, including increased resistance to nuclease degradation compared to linear oligonucleotides of the same sequence,[22] the ability to rapidly enter cells in high quantities without transfection agents,[23-24] and low immunogenicity.[25] These properties have positioned SNAs for use in applications, such as gene silencing,[26-29] immunomodulation,[30-32] drug delivery,[33-34] and mRNA detection in live cells.[35-39] However, SNAs, like many other nanomaterials, interact with serum proteins, resulting in the formation of protein coronae that can alter their uptake properties.[40] Antibody-DNA conjugates have been hybridized onto the surface of SNAs to improve their targeting capabilities and direct them to cancer cells.[17] However, in this approach, the antibody densities utilized were so low (1-2 antibodies/particle) that they would be unlikely to alter protein corona formation. Alternatively, PEGylation of the nanoparticle core has shown the ability to reduce nonspecific adsorption of serum proteins, thus extending blood circulation times, but such modifications compromise SNA uptake efficiency by targeted cells.[41]

Careful modification of a nanoparticle surface can help dictate protein corona formation and modulate its effects on pharmacokinetics, yielding constructs with improved targeting capabilities[10, 16-17] or reduced nonspecific cellular uptake.[3, 18-19]

Accordingly, in some aspects the disclosure provides a method of improving stability and/or extending blood circulation half-life of a spherical nucleic acid (SNA), the SNA comprising a nanoparticle core and one or more oligonucleotides attached to the surface of the nanoparticle core, the method comprising: adsorbing each of a plurality of proteins on the surface of the SNA via a non-covalent interaction, wherein the adsorbing results in the SNA having improved stability and/or extended blood circulation half-life relative to a control spherical nucleic acid (SNA) not adsorbed with the plurality of proteins. In some embodiments, the non-covalent interaction is an electrostatic interaction, a hydrogen bonding interaction, or a hydrophobic interaction. In some embodiments, the plurality of proteins comprises at least 5 proteins. In further embodiments, the plurality of proteins comprises from about 5 to about 50 proteins. In various embodiments, the plurality of proteins comprises a targeting protein, a dysopsonin, a complement inhibitor, or a combination thereof. In some embodiments, the targeting protein is an antibody, a cell-penetrating peptide, a nuclear localization signal peptide, or a combination thereof. In some embodiments, the antibody is a human epidermal growth factor receptor 2 (HER2) antibody, an epidermal growth factor receptor (EGFR) antibody, a human TRAIL receptor 2 antibody, or a combination thereof. In some embodiments, the dysopsonin is apolipoprotein E (ApoE), human serum albumin, immunoglobulin A (IgA), or a combination thereof. In some embodiments, the complement inhibitor is fibrinogen, factor H, or a combination thereof. In some embodiments, the targeting protein is transferrin. In some embodiments, the nanoparticle core is a metallic core, a micellar core, a dendrimer core, a liposomal core, a polymer core, a metal-organic framework core, or a combination thereof. In some embodiments, the polymer is polylactide, a polylactide-polyglycolide copolymer, a polycaprolactone, a polyacrylate, alginate, polypyrrole, polythiophene, polyaniline, polyethylenimine, poly(methyl methacrylate), poly(lactic-co-glycolic acid) (PLGA), polystyrene, or chitosan. In further embodiments, the nanoparticle core is gold, silver, platinum, aluminum, palladium, copper, cobalt, indium, cadmium selenide, iron oxide, fullerene, metal-organic framework, zinc sulfide, or nickel. In various embodiments, the one or more oligonucleotides is DNA, RNA, a modified form thereof, or a combination thereof. In some embodiments, the one or more oligonucleotides comprises an inhibitory oligonucleotide. In further embodiments, the inhibitory oligonucleotide is antisense DNA, small interfering RNA (siRNA), an aptamer, a short hairpin RNA (shRNA), a DNAzyme, or an aptazyme. In some embodiments, the one or more oligonucleotides comprises an immunostimulatory oligonucleotide. In some embodiments, the immunostimulatory oligonucleotide is double-stranded DNA (dsDNA). In some embodiments, the immunostimulatory oligonucleotide is a toll-like receptor (TLR) agonist. In further embodiments, the TLR agonist is a toll-like receptor 1 (TLR-1) agonist, toll-like receptor 2 (TLR-2) agonist, toll-like receptor 3 (TLR-3) agonist, toll-like receptor 4 (TLR-4) agonist, toll-like receptor 5 (TLR-5) agonist, toll-like receptor 6 (TLR-6) agonist, toll-like receptor 7 (TLR-7) agonist, toll-like receptor 8 (TLR-8) agonist, toll-like receptor 9 (TLR-9) agonist, toll-like receptor 10 (TLR-10) agonist, toll-like receptor 11 (TLR-11) agonist, toll-like receptor 12 (TLR-12) agonist, toll-like receptor 13 (TLR-13) agonist, or a combination thereof. In some embodiments, the one or more oligonucleotides comprises a toll-like receptor (TLR) antagonist. In further embodiments, the TLR-antagonist is a toll-like receptor 1 (TLR-1) antagonist, toll-like receptor 2 (TLR-2) antagonist, toll-like receptor 3 (TLR-3) antagonist, toll-like receptor 4 (TLR-4) antagonist, toll-like receptor 5 (TLR-5) antagonist, toll-like receptor 6 (TLR-6) antagonist, toll-like receptor 7 (TLR-7) antagonist, toll-like receptor 8 (TLR-8) antagonist, toll-like receptor 9 (TLR-9) antagonist, toll-like receptor 10 (TLR-10) antagonist, toll-like receptor 11 (TLR-11) antagonist, toll-like receptor 12 (TLR-12) antagonist, toll-like receptor 13 (TLR-13) antagonist, or a combination thereof. In various embodiments, a method of the disclosure further comprises administering the SNA to a subject.

In some aspects, the disclosure provides a spherical nucleic acid (SNA) comprising a protein corona, wherein the SNA comprises (i) a nanoparticle core and (ii) one or more oligonucleotides attached to the surface of the nanoparticle core; and wherein the protein corona comprises a plurality of proteins, wherein each of the plurality of proteins is adsorbed on the surface of the SNA via a non-covalent interaction.

DETAILED DESCRIPTION

Figure 1:
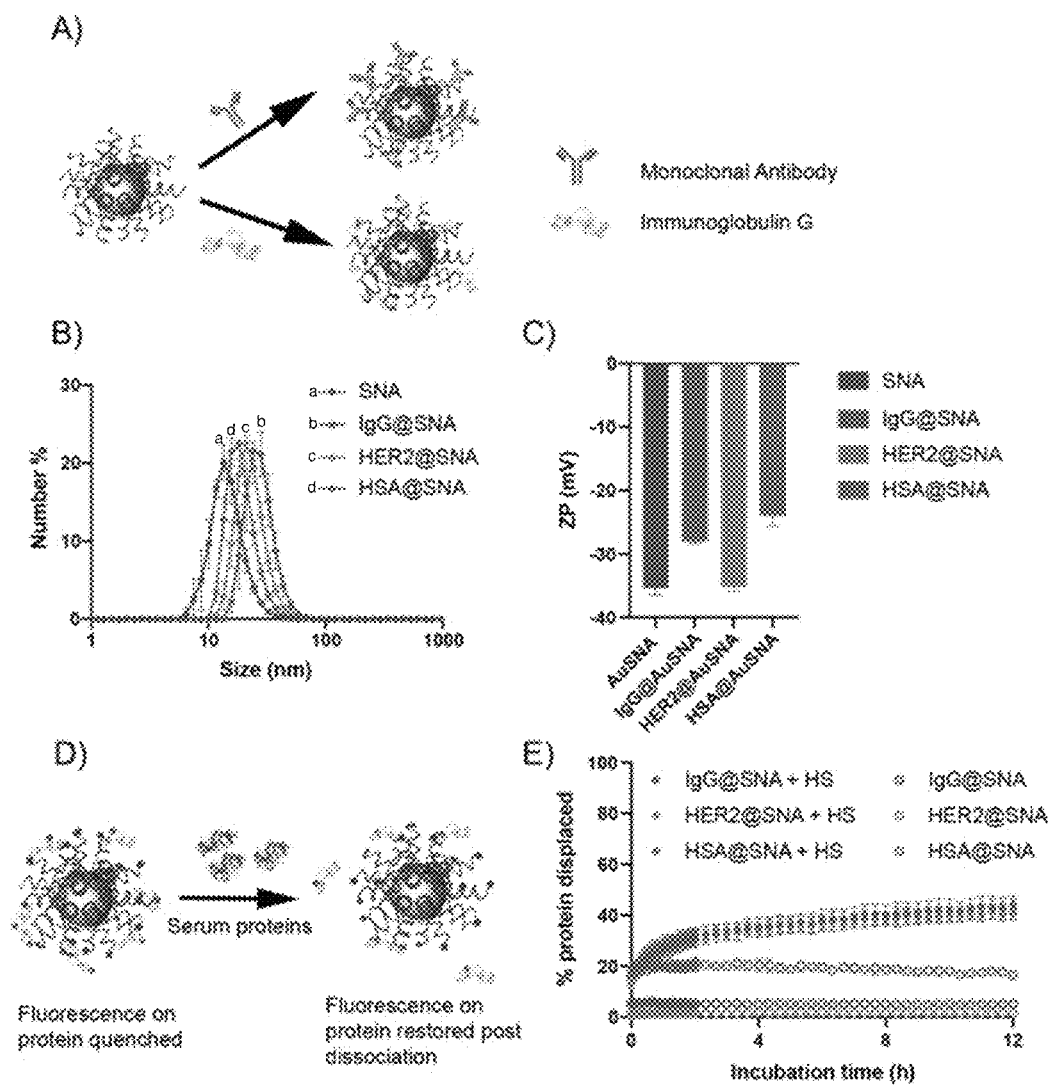
FIG. 1 depicts the synthesis and characterization of protein-adsorbed SNAs. (A) Schematic representation of monoclonal antibody (top) or IgG (bottom) immobilization on the oligonucleotide shell of SNAs. (B) Distributions of the hydrodynamic diameter of SNAs, IgG-immobilized SNAs (IgG@SNA), anti-HER2-immobilized SNAs (HER2@SNA), and HSA-immobilized SNAs (HSA@SNA). (C) Zeta potential of the SNAs, IgG-immobilized SNAs, anti-HER2-immobilized SNAs, and HSA-immobilized SNAs. (D) Schematics of the Texas Red-X-labeled proteins displaced from the surface of Cy5-labeled SNAs by serum proteins. Fluorescence of Texas Red-X increases as protein displacement occurs. (E) Kinetic fluorescence profile of Texas Red-X-labeled IgG, anti-HER2, or HSA during incubation with serum proteins.

Spherical nucleic acids (SNAs) are nanomaterials typically comprising a nanoparticle core (for example and without limitation, a liposomal core or an inorganic (e.g., metallic) core) and a functional, dense, and highly oriented oligonucleotide shell with unusual biological properties that make them appealing for many applications, including sequence-specific gene silencing, mRNA quantification, and immunostimulation. When placed in biological fluids, SNAs readily interact with serum proteins, leading to the formation of ill-defined protein coronae on the surface, which can influence the targeting capabilities of the conjugate. Herein, SNAs are designed and synthesized with functional proteins, such as antibodies and serum albumin, deliberately adsorbed onto their surfaces. These particles, compared to native SNAs, exhibit increased resistance to protease degradation, but still remain functional as they can engage in hybridization with complementary oligonucleotides.

Exemplary applications of the subject matter of the disclosure include, but are not limited to:

Structures can be used to render targeting capabilities for selected cell populations Create active protein coronae for improving the biological properties of SNAs Advantages of the subject matter of the disclosure include, but are not limited to:

It offers an easy and flexible approach to SNA modification for cellular selectivity.

The pre-adsorbed protein coronae remains functional in the presence of serum.

The pre-adsorbed protein coronae protect the oligonucleotides on the nanoparticle surface from fast digestion by endonucleases.

Regardless of the protein corona, oligonucleotides on the SNAs still remain accessible.

In any of the aspects or embodiments of the disclosure, an easy and flexible approach to improve the targeting capabilities of SNAs is provided. Meanwhile, any active protein can be coated onto SNA surface, such that multiple functions can be obtained. For example and without limitation, serum albumin, an identified dysopsonin, can be pre-adsorbed onto the SNA surface and partially shield SNAs from fast clearance by macrophages, which are one of the main components of the mononuclear phagocyte system.

In any of the aspects or embodiments of the disclosure, compositions and methods are provided to add an active protein layer to SNAs for improved stability, targeting, and biodistribution properties. Nanoparticles comprising targeting groups must possess the ability to remain functional in biological fluids, and the compositions of the present disclosure possess this ability through physically adsorbing targeting groups on the nanoparticle surface.

As used in this specification and the appended claims, the singular forms "a," "an," and "the" include plural reference unless the context clearly dictates otherwise.

The terms "polynucleotide" and "oligonucleotide" are interchangeable as used herein.

As used herein, the term "about," when used to modify a particular value or range, generally means within 20 percent, e.g., within 10 percent, 5 percent, 4 percent, 3 percent, 2 percent, or 1 percent of the stated value or range.

Unless otherwise stated, all ranges contemplated herein include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

Protein Adsorption on Spherical Nucleic Acids (SNAs)

In any of the aspects or embodiments of the disclosure, spherical nucleic acids (SNAs) comprising tailored and active protein coronae are provided. A SNA of the disclosure is designed and synthesized with a plurality of functional proteins deliberately adsorbed onto its surface to form a protein corona. As used herein, a "functional" protein is a protein that imparts targeting capabilities to SNAs, or reduces nonspecific clearance of SNAs by the mononuclear phagocyte system. Accordingly, in some aspects the disclosure provides a spherical nucleic acid (SNA) comprising a protein corona, wherein the SNA comprises (i) a nanoparticle core and (ii) one or more oligonucleotides attached to the surface of the nanoparticle core; and wherein the protein corona comprises a plurality of proteins, wherein each of the plurality of proteins is adsorbed on the surface of the SNA via a non-covalent interaction.

In further aspects, the disclosure provides a method of improving stability and/or extending blood circulation half-life of a spherical nucleic acid (SNA), the SNA comprising a nanoparticle core and one or more oligonucleotides attached to the surface of the nanoparticle core, the method comprising adsorbing each of a plurality of proteins on the surface of the SNA via a non-covalent interaction, wherein the adsorbing results in the SNA having improved stability and/or extended blood circulation half-life relative to a substantially identical spherical nucleic acid (SNA) not adsorbed with the plurality of proteins. In any of the aspects or embodiments of the disclosure, the adsorption is non-covalent adsorption. In various embodiments, the adsorption is electrostatic adsorption, hydrophobic adsorption, adsorption through hydrogen bonding, or a combination thereof. In general, the protein corona is created by incubating a SNA with a plurality functional proteins (e.g., dysopsonins and/or targeting proteins). In various embodiments, the plurality of proteins comprises at least 5 proteins. In further embodiments, the plurality of proteins comprises about 5 to about 50 proteins. In still further embodiments, the plurality of proteins comprises about 5 to about 40, about 5 to about 30, about 5 to about 20, or about 5 to about 10 proteins. In some embodiments, the plurality of proteins comprises about 10 to about 50, about 10 to about 40, about 10 to about 30, or about 10 to about 20 proteins. In further embodiments, the plurality of proteins comprises about or at least about 5, about or at least about 10, about or at least about 15, about or at least about 20, about or at least about 25, about or at least about 30, about or at least about 35, about or at least about 40, about or at least about 45, or about or at least about 50 proteins. In some embodiments, the plurality of proteins comprises less than 50 but at least 5, less than 45 but at least 5, less than 40 but at least 5, less than 35 but at least 5, less than 30 but at least 5, less than 25 but at least 5, less than 20 but at least 5, less than 15 but at least 5, or less than 10 but at least 5 proteins.

The plurality of proteins adsorbed on the surface of a SNA is selected based on the particular application(s) of interest. In various embodiments, the plurality of proteins comprises a targeting protein, a dysopsonin, a complement inhibitor, or a combination thereof. By way of example, one would select which proteins to be adsorbed and the plurality based on the intended function of the resulting SNAs. For example and without limitation, if a HER2-neutralizing SNA is to be administered intravenously, a combination of HER2-targeting protein (e.g., trastuzumab) and dysopsonin (e.g., albumin) can be adsorbed onto SNA surface. The plurality of each protein can be determined experimentally. In some embodiments, dysopsonins are adsorbed onto the SNA surface thereby partially shielding the SNA from fast clearance by macrophages. This results in increased blood circulation half-life of the SNA relative to a substantially identical SNA on which dysopsonins were not adsorbed.

The plurality of proteins can include proteins that are naturally occurring and/or non-naturally occurring. Naturally occurring proteins include without limitation biologically active proteins (including antibodies) that exist in nature or can be produced in a form that is found in nature by, for example, chemical synthesis or recombinant expression techniques. Naturally occurring proteins also include lipoproteins and post-translationally modified proteins, such as, for example and without limitation, glycosylated proteins. Antibodies contemplated for use in the methods and compositions of the present disclosure include without limitation antibodies that recognize and associate with a target molecule either in vivo or in vitro.

Non-naturally occurring proteins contemplated by the present disclosure include but are not limited to synthetic proteins, as well as fragments, analogs and variants of naturally occurring or non-naturally occurring proteins as defined herein. Non-naturally occurring proteins also include proteins or protein substances that have D-amino acids, modified, derivatized, or non-naturally occurring amino acids in the D- or L-configuration and/or peptidomimetic units as part of their structure. The term "peptide" typically refers to short (e.g., about 2-50 amino acids in length) polypeptides/proteins. Non-naturally occurring proteins are prepared, for example, using an automated protein synthesizer or, alternatively, using recombinant expression techniques using a modified polynucleotide which encodes the desired protein.

Fragments, analogs, and variants of proteins are also contemplated herein. As used herein a "fragment" of a protein is meant to refer to any portion of a protein smaller than the full-length protein or protein expression product. As used herein an "analog" refers to any of two or more proteins substantially similar in structure and having the same biological activity, but can have varying degrees of activity, to either the entire molecule, or to a fragment thereof. Analogs differ in the composition of their amino acid sequences based on one or more mutations involving substitution, deletion, insertion and/or addition of one or more amino acids for other amino acids. Substitutions can be conservative or non-conservative based on the physico-chemical or functional relatedness of the amino acid that is being replaced and the amino acid replacing it. As used herein a "variant" refers to a protein or analog thereof that is modified to comprise additional chemical moieties not normally a part of the molecule. Such moieties may modulate, for example and without limitation, the molecule's solubility, absorption, and/or biological half-life. Moieties capable of mediating such effects are disclosed in Remington's Pharmaceutical Sciences (1980). Procedures for coupling such moieties to a molecule are well known in the art. In various aspects, proteins are modified by glycosylation, PEGylation, and/or polysialylation.

Fusion proteins, including fusion proteins wherein one fusion component is a fragment or a mimetic, are also contemplated. A "mimetic" as used herein means a peptide or protein having a biological activity that is comparable to the protein of which it is a mimetic. By way of example, an endothelial growth factor mimetic is a peptide or protein that has a biological activity comparable to the native endothelial growth factor. The term further includes peptides or proteins that indirectly mimic the activity of a protein of interest, such as by potentiating the effects of the natural ligand of the protein of interest.

Targeting proteins include antibodies along with fragments and derivatives thereof, including but not limited to Fab fragments, F(ab')$_2$ fragments, Fv fragments, Fc fragments, one or more complementarity determining regions (CDR) fragments, individual heavy chains, individual light chain, dimeric heavy and light chains (as opposed to heterotetrameric heavy and light chains found in an intact antibody, single chain antibodies (scAb), humanized antibodies (as well as antibodies modified in the manner of humanized antibodies but with the resulting antibody more closely resembling an antibody in a non-human species), chelating recombinant antibodies (CRABs), bispecific antibodies and multispecific antibodies, and other antibody derivative or fragments known in the art.

In various embodiments, the targeting protein is an antibody, a cell-penetrating peptide, a nuclear localization signal peptide or a combination thereof. Proteins that target certain receptors (e.g., transferrin) are also contemplated by the disclosure. Any antibody may be used in the methods described herein. In various embodiments, antibodies contemplated by the disclosure include, but are not limited to, a human epidermal growth factor receptor 2 (HER2) antibody (e.g., trastuzumab, pertuzumab), an epidermal growth factor receptor (EGFR) antibody (e.g., cetuximab, necitumumab, panitumumab), a human TRAIL receptor 2 antibody (e.g., conatumumab), or a combination thereof.

As described above, dysopsonins can partially shield a SNA from fast clearance by macrophages. Dysopsonins contemplated by the disclosure include, in various embodiments, apolipoprotein E (ApoE), human serum albumin, Immunoglobulin A (IgA), or a combination thereof.

Complement inhibitors contemplated by the disclosure include, without limitation, fibrinogen and factor H.

In various aspects, the disclosure provides methods of improving stability and/or extending blood circulation half-life of a spherical nucleic acid (SNA), the SNA comprising a nanoparticle core and one or more oligonucleotides attached to the surface of the nanoparticle core, the method comprising adsorbing each of a plurality of proteins on the surface of the SNA via a non-covalent interaction, wherein the adsorbing results in the SNA having improved stability and/or extended blood circulation half-life relative to a control spherical nucleic acid (SNA) not adsorbed with the plurality of proteins. By adsorbing targeting proteins to the surface of the SNA, the SNA is also contemplated to exhibit increased uptake by target cells relative to a SNA not adsorbed with the targeting proteins. Likewise, by adsorbing dysopsonin to the surface of a SNA, the SNA gains extended blood circulation half-life compared to the SNA without dysopsonin adsorbed. Methods of evaluating blood circulation half-life are known in the art and include, for example, intravenous administration of a SNA to a wild-type mouse. Several time points post-injection, blood is collected either retro-orbitally or through cardiac puncture. The amount of SNAs in each collected blood sample is then quantified by ICP-MS (for SNAs with metallic cores) or in vivo imaging system (for any SNA with fluorophore labels).

Spherical Nucleic Acids (SNAs)

As described herein, spherical nucleic acids (SNAs) are a unique class of nanomaterials comprising a spherical nanoparticle core functionalized with a highly oriented oligonucleotide shell. The oligonucleotide shell comprises one or more oligonucleotides attached to the external surface of the nanoparticle core. The nanoparticle core can either be organic (e.g., a liposome), inorganic (e.g., gold, silver, or platinum), or hollow (e.g., silica-based). The spherical architecture of the polynucleotide shell confers unique advantages over traditional nucleic acid delivery methods, including entry into nearly all cells independent of transfection agents and resistance to nuclease degradation. Furthermore, SNAs can penetrate biological barriers, including the blood-brain (see, e.g., U.S. Patent Application Publication No.

2015/0031745, incorporated by reference herein in its entirety) and blood-tumor barriers as well as the epidermis (see, e.g., U.S. Patent Application Publication No. 2010/0233270, incorporated by reference herein in its entirety).

Nanoparticles are therefore provided which are functionalized to have a polynucleotide attached thereto. In general, nanoparticles contemplated include any compound or substance with a loading capacity for a polynucleotide as described herein, including for example and without limitation, a metal, a semiconductor, a liposomal particle, a polymer-based particle (e.g., a poly (lactic-co-glycolic acid) (PLGA) particle), insulator particle compositions, and a dendrimer (organic versus inorganic). In some embodiments, the nanoparticle core is a metallic core, a micellar core, a dendrimer core, a liposomal core, a polymer core, a metal-organic framework core, or a combination thereof.

Thus, nanoparticles are contemplated which comprise a variety of inorganic materials including, but not limited to, metals, semi-conductor materials or an insulator (e.g., ceramics) as described in U.S. Patent Publication No 20030147966. For example, metal-based nanoparticles include those described herein. Ceramic nanoparticle materials include, but are not limited to, brushite, tricalcium phosphate, alumina, silica, and zirconia. Organic materials from which nanoparticles are produced include carbon. Nanoparticle polymers include polystyrene, silicone rubber, polycarbonate, polyurethanes, polypropylenes, polymethylmethacrylate, polyvinyl chloride, polyesters, polyethers, and polyethylene. In further embodiments, the polymer is polylactide, a polylactide-polyglycolide copolymer, a polycaprolactone, a polyacrylate, alginate, polypyrrole, polythiophene, polyaniline, polyethylenimine, poly(methyl methacrylate), poly(lactic-co-glycolic acid) (PLGA), polystyrene, or chitosan. Biodegradable, biopolymer (e.g., polypeptides such as BSA, polysaccharides, etc.), other biological materials (e.g., carbohydrates), and/or polymeric compounds are also contemplated for use in producing nanoparticles.

Liposomal particles, for example as disclosed in International Patent Application No. PCT/US2014/068429 (incorporated by reference herein in its entirety, particularly with respect to the discussion of liposomal particles) are also contemplated by the disclosure. Hollow particles, for example as described in U.S. Patent Publication Number 2012/0282186 (incorporated by reference herein in its entirety) are also contemplated herein. Liposomal particles of the disclosure have at least a substantially spherical geometry, an internal side and an external side, and comprise a lipid bilayer. The lipid bilayer comprises, in various embodiments, a lipid from the phosphocholine family of lipids or the phosphoethanolamine family of lipids. While not meant to be limiting, the first-lipid is chosen from group consisting of 1,2-dioleoyl-sn-glycero-3-phosphocholine (DOPC), 1,2-dimyristoyl-sn-phosphatidylcholine (DMPC), 1-palmitoyl-2-oleoyl-sn-phosphatidylcholine (POPC), 1,2-distearoyl-sn-glycero-3-phospho-(1'-rac-glycerol) (DSPG), 1,2-dioleoyl-sn-glycero-3-phospho-(1'-rac-glycerol) (DOPG), 1,2-distearoyl-sn-glycero-3-phosphocholine (DSPC), 1,2-dipalmitoyl-sn-glycero-3-phosphocholine (DPPC), 1,2-di-(9Z-octadecenoyl)-sn-glycero-3-phosphoethanolamine (DOPE), 1,2-dihexadecanoyl-sn-glycero-3-phosphoethanolamine (DPPE), 1,2-dioleoyl-sn-glycero-3-phospho-(1'-rac-glycerol) (DOPG), 1,2-distearoyl-sn-glycero-3-phosphoethanolamine (DSPE), cardiolipin, lipid A, and a combination thereof.

In some embodiments, the nanoparticle is metallic, and in various aspects, the nanoparticle is a colloidal metal. Thus, in various embodiments, nanoparticles useful in the compositions and methods of the disclosure include metal (including for example and without limitation, gold, silver, platinum, aluminum, palladium, copper, cobalt, indium, cadmium selenide, iron oxide, fullerene, metal-organic framework, zinc sulfide, nickel, or any other metal amenable to nanoparticle formation), semiconductor (including for example and without limitation, CdSe, CdS, and CdS or CdSe coated with ZnS) and magnetic (for example, ferromagnetite) colloidal materials. Other nanoparticles useful in the compositions and methods of the disclosure include, also without limitation, ZnS, ZnO, Ti, $TiO_2$, Sn, $SnO_2$, Si, $SiO_2$, Fe, $Fe^{4+}$, Ag, Cu, Ni, Al, steel, cobalt-chrome alloys, Cd, titanium alloys, AgI, AgBr, $HgI_2$, PbS, PbSe, ZnTe, CdTe, $In_2S_3$, $In_2Se_3$, $Cd_3P_2$, $Cd_3As_2$, InAs, and GaAs. Methods of making ZnS, ZnO, $TiO_2$, AgI, AgBr, $HgI_2$, PbS, PbSe, ZnTe, CdTe, $In_2S_3$, $In_2Se_3$, $Cd_3P_2$, $Cd_3As_2$, InAs, and GaAs nanoparticles are also known in the art. See, e.g., Weller, Angew. Chem. Int. Ed. Engl., 32, 41 (1993); Henglein, Top. Curr. Chem., 143, 113 (1988); Henglein, Chem. Rev., 89, 1861 (1989); Brus, Appl. Phys. A., 53, 465 (1991); Bahncmann, in Photochemical Conversion and Storage of Solar Energy (eds. Pelizetti and Schiavello 1991), page 251; Wang and Herron, J. Phys. Chem., 95, 525 (1991); Olshavsky, et al., J. Am. Chem. Soc., 112, 9438 (1990); Ushida et al., J. Phys. Chem., 95, 5382 (1992). In some embodiments, the nanoparticle is an iron oxide nanoparticle.

Methods of making metal, semiconductor and magnetic nanoparticles are well-known in the art. See, for example, Schmid, G. (ed.) Clusters and Colloids (VCH, Weinheim, 1994); Hayat, M. A. (ed.) Colloidal Gold: Principles, Methods, and Applications (Academic Press, San Diego, 1991); Massart, R., IEEE Transactions On Magnetics, 17, 1247 (1981); Ahmadi, T. S. et al., Science, 272, 1924 (1996); Henglein, A. et al., J. Phys. Chem., 99, 14129 (1995); Curtis, A. C., et al., Angew. Chem. Int. Ed. Engl., 27, 1530 (1988). Preparation of polyalkylcyanoacrylate nanoparticles prepared is described in Fattal, et al., J. Controlled Release (1998) 53: 137-143 and U.S. Pat. No. 4,489,055. Methods for making nanoparticles comprising poly(D-glucaramidoamine)s are described in Liu, et al., J. Am. Chem. Soc. (2004) 126:7422-7423. Preparation of nanoparticles comprising polymerized methylmethacrylate (MMA) is described in Tondelli, et al., Nucl. Acids Res. (1998) 26:5425-5431, and preparation of dendrimer nanoparticles is described in, for example Kukowska-Latallo, et al., Proc. Natl. Acad. Sci. USA (1996) 93:4897-4902 (Starburst polyamidoamine dendrimers).

Suitable nanoparticles are also commercially available from, for example, Ted Pella, Inc. (gold), Amersham Corporation (gold) and Nanoprobes, Inc. (gold).

Also as described in US Patent Publication No. 20030147966, nanoparticles comprising materials described herein are available commercially or they can be produced from progressive nucleation in solution (e.g., by colloid reaction), or by various physical and chemical vapor deposition processes, such as sputter deposition. See, e.g., HaVashi, (1987) Vac. Sci. Technol. July/August 1987, A5(4):1375-84; Hayashi, (1987) Physics Today, December 1987, pp. 44-60; MRS Bulletin, January 1990, pgs. 16-47.

As further described in U.S. Patent Publication No. 20030147966, nanoparticles contemplated are produced using $HAuCl_4$ and a citrate-reducing agent, using methods known in the art. See, e.g., Marinakos et al., (1999) Adv. Mater. 11: 34-37; Marinakos et al., (1998) Chem. Mater. 10: 1214-19; Enustun & Turkevich, (1963) J. Am. Chem. Soc. 85: 3317. Tin oxide nanoparticles having a dispersed aggregate particle size of about 140 nm are available commercially from Vacuum Metallurgical Co., Ltd. of Chiba, Japan. Other commercially available nanoparticles of various compositions and size ranges are available, for example, from Vector Laboratories, Inc. of Burlingame, Calif.

Nanoparticles can range in size from about 1 nm to about 250 nm in mean diameter, about 1 nm to about 240 nm in mean diameter, about 1 nm to about 230 nm in mean diameter, about 1 nm to about 220 nm in mean diameter, about 1 nm to about 210 nm in mean diameter, about 1 nm to about 200 nm in mean diameter, about 1 nm to about 190 nm in mean diameter, about 1 nm to about 180 nm in mean diameter, about 1 nm to about 170 nm in mean diameter, about 1 nm to about 160 nm in mean diameter, about 1 nm to about 150 nm in mean diameter, about 1 nm to about 140 nm in mean diameter, about 1 nm to about 130 nm in mean diameter, about 1 nm to about 120 nm in mean diameter, about 1 nm to about 110 nm in mean diameter, about 1 nm to about 100 nm in mean diameter, about 1 nm to about 90 nm in mean diameter, about 1 nm to about 80 nm in mean diameter, about 1 nm to about 70 nm in mean diameter, about 1 nm to about 60 nm in mean diameter, about 1 nm to about 50 nm in mean diameter, about 1 nm to about 40 nm in mean diameter, about 1 nm to about 30 nm in mean diameter, or about 1 nm to about 20 nm in mean diameter, about 1 nm to about 10 nm in mean diameter. In other aspects, the size of the nanoparticles is from about 5 nm to about 150 nm (mean diameter), from about 5 to about 50 nm, from about 10 to about 30 nm, from about 10 to 150 nm, from about 10 to about 100 nm, or about 10 to about 50 nm. The size of the nanoparticles is from about 5 nm to about 150 nm (mean diameter), from about 30 to about 100 nm, from about 40 to about 80 nm. The size of the nanoparticles used in a method varies as required by their particular use or application. The variation of size is advantageously used to optimize certain physical characteristics of the nanoparticles, for example, optical properties or the amount of surface area that can be functionalized as described herein. In further embodiments, a plurality of SNAs (e.g., liposomal particles) is produced and the SNAs in the plurality have a mean diameter of less than or equal to about 100 nanometers (e.g., about 5 nanometers to about 100 nanometers), or less than or equal to about 50 nanometers (e.g., about 5 nanometers to about 50 nanometers, or about 5 nanometers to about 40 nanometers, or about 5 nanometers to about 30 nanometers, or about 5 nanometers to about 20 nanometers, or about 10 nanometers to about 50 nanometers, or about 10 nanometers to about 40 nanometers, or about 10 nanometers to about 30 nanometers, or about 10 nanometers to about 20 nanometers). In further embodiments, the SNAs in the plurality created by a method of the disclosure have a mean diameter of less than or equal to about 20 nanometers, or less than or equal to about 25 nanometers, or less than or equal to about 30 nanometers, or less than or equal to about 35 nanometers, or less than or equal to about 40 nanometers, or less than or equal to about 45 nanometers, or less than or equal to about 50 nanometers, or less than or equal to about 55 nanometers, or less than or equal to about 60 nanometers.

Oligonucleotides

The disclosure provides spherical nucleic acids (SNAs) comprising a nanoparticle core and one or more oligonucleotides attached thereto. In any of the aspects or embodiments of the disclosure, the SNA comprises a nanoparticle core and a plurality of oligonucleotides attached thereto. SNAs comprise, in various aspects and embodiments of the disclosure, DNA oligonucleotides, RNA oligonucleotides, or a combination thereof, attached to the surface of the nanoparticle core of the SNA. In various embodiments, an oligonucleotide is single-stranded, double-stranded, or partially double-stranded. Modified forms of oligonucleotides are also contemplated which include those having at least one modified internucleotide linkage. In some embodiments, the oligonucleotide is all or in part a peptide nucleic acid. Other modified internucleoside linkages include at least one phosphorothioate linkage. Still other modified oligonucleotides include those comprising one or more universal bases. "Universal base" refers to molecules capable of substituting for binding to any one of A, C, G, T and U in nucleic acids by forming hydrogen bonds without significant structure destabilization. The oligonucleotide incorporated with the universal base analogues is able to function, e.g., as a probe in hybridization. Examples of universal bases include but are not limited to 5'-nitroindole-2'-deoxyriboside, 3-nitropyrrole, inosine and hypoxanthine.

The term "nucleotide" or its plural as used herein is interchangeable with modified forms as discussed herein and otherwise known in the art. The term "nucleobase" or its plural as used herein is interchangeable with modified forms as discussed herein and otherwise known in the art. Nucleotides or nucleobases comprise the naturally occurring nucleobases A, G, C, T, and U. Non-naturally occurring nucleobases include, for example and without limitations, xanthine, diaminopurine, 8-oxo-N6-methyladenine, 7-deazaxanthine, 7-deazaguanine, N4,N4-ethanocytosin, N',N'-ethano-2,6-diaminopurine, 5-methylcytosine (mC), 5-(C3-C6)-alkynyl-cytosine, 5-fluorouracil, 5-bromouracil, pseudoisocytosine, 2-hydroxy-5-methyl-4-tr-iazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). In various aspects, oligonucleotides also include one or more "nucleosidic bases" or "base units" which are a category of non-naturally-occurring nucleotides that include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

Examples of oligonucleotides include those containing modified backbones or non-natural internucleoside linkages. Oligonucleotides having modified backbones include those that retain a phosphorus atom in the backbone and those that do not have a phosphorus atom in the backbone. Modified oligonucleotides that do not have a phosphorus atom in their internucleoside backbone are considered to be within the meaning of "oligonucleotide".

Modified oligonucleotide backbones containing a phosphorus atom include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2'linkage. Also contemplated are oligonucleotides having inverted polarity comprising a single 3' to 3' linkage at the 3'-most internucleotide linkage, i.e. a single inverted nucleoside residue which may be abasic (the nucleotide is missing or has a hydroxyl group in place thereof). Salts, mixed salts and free acid forms are also contemplated. Representative United States patents that teach the preparation of the above phosphorus-containing linkages include, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, the disclosures of which are incorporated by reference herein.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages; siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. See, for example, U.S. Pat. Nos. 5,034,506; 5,166,315; 5,185,444; 5,214,134; 5,216, 141; 5,235,033; 5,264,562; 5,264,564; 5,405,938; 5,434, 257; 5,466,677; 5,470,967; 5,489,677; 5,541,307; 5,561, 225; 5,596,086; 5,602,240; 5,610,289; 5,602,240; 5,608, 046; 5,610,289; 5,618,704; 5,623,070; 5,663,312; 5,633, 360; 5,677,437; 5,792,608; 5,646,269 and 5,677,439, the disclosures of which are incorporated herein by reference in their entireties.

In still further embodiments, oligonucleotide mimetics wherein both one or more sugar and/or one or more internucleotide linkage of the nucleotide units are replaced with "non-naturally occurring" groups. The bases of the oligonucleotide are maintained for hybridization. In some aspects, this embodiment contemplates a peptide nucleic acid (PNA). In PNA compounds, the sugar-backbone of an oligonucleotide is replaced with an amide containing backbone. See, for example U.S. Pat. Nos. 5,539,082; 5,714,331; and 5,719,262, and Nielsen et al., Science, 1991, 254, 1497-1500, the disclosures of which are herein incorporated by reference.

In still further embodiments, oligonucleotides are provided with phosphorothioate backbones and oligonucleosides with heteroatom backbones, and including —$CH_2$—NH—O—$CH_2$—, —$CH_2$—N($CH_3$)—O—$CH_2$—, —$CH_2$—O—N($CH_3$)—$CH_2$—, —$CH_2$—N($CH_3$)—N($CH_3$)—$CH_2$— and —O—N($CH_3$)—$CH_2$—$CH_2$— described in U.S. Pat. Nos. 5,489,677, and 5,602,240. Also contemplated are oligonucleotides with morpholino backbone structures described in U.S. Pat. No. 5,034,506.

In various forms, the linkage between two successive monomers in the oligonucleotide consists of 2 to 4, desirably 3, groups/atoms selected from —$CH_2$—, —O—, —S—, —$NR^H$—, >C=O, >C=$NR^H$, >C=S, —Si(R")$_2$—, —SO—, —S(O)$_2$—, —P(O)$_2$—, —PO(BH$_3$)—, —P(O,S)—, —P(S)$_2$—, —PO(R")—, —PO(OCH$_3$)—, and —PO(NHR$^H$)—, where R$^H$ is selected from hydrogen and $C_{1-4}$-alkyl, and R" is selected from $C_{1-6}$-alkyl and phenyl. Illustrative examples of such linkages are —$CH_2$—$CH_2$—$CH_2$—, —$CH_2$—CO—$CH_2$—, —$CH_2$—CHOH—$CH_2$—, —O—$CH_2$—O—, —O—$CH_2$—$CH_2$—, —O—$CH_2$—CH=(including R$^5$ when used as a linkage to a succeeding monomer), —$CH_2$—$CH_2$—O—, —$NR^H$—$CH_2$—$CH_2$—, —$CH_2$—$CH_2$—$NR^H$—, —$CH_2$—$NR^H$—$CH_2$—, —O—$CH_2$—$CH_2$—$NR^H$—, —$NR^H$—CO—O—, —$NR^H$—CO—$NR^H$—, —$NR^H$—CS—$NR^H$—, —$NR^H$—C(=$NR^H$)—$NR^H$—, —$NR^H$—CO—$CH_2$—$NR^H$—O—CO—O—, —O—CO—$CH_2$—O—, —O—$CH_2$—CO—O—, —$CH_2$—CO—$NR^H$—, —O—CO—$NR^H$—, —$NR^H$—CO—$CH_2$—, —O—$CH_2$—CO—$NR^H$—, —O—$CH_2$—$CH_2$—$NR^H$—, —CH=N—O—, —$CH_2$—$NR^H$—O—, —$CH_2$—O—N=(including R$^5$ when used as a linkage to a succeeding monomer), —$CH_2$—O—$NR^H$—, —CO—$NR^H$—$CH_2$—, —$CH_2$—$NR^H$—O—, —$CH_2$—$NR^H$—CO—, —O—$NR^H$—$CH_2$—, —O—$NR^H$—, —O—$CH_2$—S—, —S—$CH_2$—O—, —$CH_2$—$CH_2$—S—, —O—$CH_2$—$CH_2$—S—, —S—$CH_2$—CH=(including R$^5$ when used as a linkage to a succeeding monomer), —S—$CH_2$—$CH_2$—, —S—$CH_2$—$CH_2$—O—, —S—$CH_2$—$CH_2$—S—, —$CH_2$—S—$CH_2$—, —$CH_2$—SO—$CH_2$—, —$CH_2$—$SO_2$—$CH_2$—, —O—SO—O—, —O—S(O)$_2$—O—, —O—S(O)$_2$—$CH_2$—, —O—S(O)$_2$—$NR^H$—, —$NR^H$—S(O)$_2$—$CH_2$—; —O—S(O)$_2$—$CH_2$—, —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —O—P(S)$_2$—S—, —S—P(O)$_2$—S—, —S—P(O,S)—S—, —O—PO(R")—O—, —O—PO(OCH$_3$)—O—, —O—PO(O $CH_2CH_3$)—O—, —O—PO(O $CH_2CH_2$S—R)—O—, —O—PO(BH$_3$)—O—, —O—PO(NHR$^N$)—O—, —O—P(O)$_2$—$NR^H$ H—, —$NR^H$—P(O)$_2$—O—, —O—P(O,$NR^H$)—O—, —$CH_2$—P(O)$_2$—O—, —O—P(O)$_2$—$CH_2$—, and —O—Si(R")$_2$—O—; among which —$CH_2$—CO—$NR^H$—, —$CH_2$—$NR^H$—O—, —S—$CH_2$—O—, —O—P(O)$_2$—O—O—P(—O,S)—O—, —O—P(S)$_2$—O—, —$NR^H$ P(O)$_2$—O—, —O—P(O,$NR^H$)—O—, —O—PO(R")—O—, —O—PO(CH$_3$)—O—, and —O—PO(NHR$^N$)—O—, where R$^H$ is selected form hydrogen and $C_{1-4}$-alkyl, and R" is selected from $C_{1-6}$-alkyl and phenyl, are contemplated. Further illustrative examples are given in Mesmaeker et. al., Current Opinion in Structural Biology 1995, 5, 343-355 and Susan M. Freier and Karl-Heinz Altmann, Nucleic Acids Research, 1997, vol 25, pp 4429-4443.

Still other modified forms of oligonucleotides are described in detail in U.S. patent application No. 20040219565, the disclosure of which is incorporated by reference herein in its entirety.

Modified oligonucleotides may also contain one or more substituted sugar moieties. In certain aspects, oligonucleotides comprise one of the following at the 2' position: OH;

F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Other embodiments include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH2, heterocycloalkyl, heterocycloalkaryl, aminoalkylamino, polyalkylamino, substituted silyl, or an RNA cleaving group. In some embodiments, a modification includes 2'-methoxyethoxy (2'-O—CH$_2$CH$_2$OCH$_3$, also known as 2'-O-(2-methoxyethyl) or 2'-MOE) (Martin et al., Helv. Chim. Acta, 1995, 78, 486-504) i.e., an alkoxyalkoxy group. Other modifications include 2'-dimethylaminooxyethoxy, i.e., a O(CH$_2$)$_2$ON(CH$_3$)$_2$ group, also known as 2'-DMAOE, and 2'-dimethylaminoethoxyethoxy (also known in the art as 2'-O-dimethylamino-ethoxy-ethyl or 2'-DMAEOE), i.e., 2'-O—CH$_2$—O—CH$_2$—N(CH$_3$)$_2$.

Still other modifications include 2'-methoxy (2'-O—CH$_3$), 2'-aminopropoxy (2'-OCH$_2$CH$_2$CH$_2$NH$_2$), 2'-allyl (2'-CH$_2$—CH═CH$_2$), 2'-O-allyl (2'-O—CH$_2$—CH═CH$_2$) and 2'-fluoro (2'-F). The 2'-modification may be in the arabino (up) position or ribo (down) position. In one aspect, a 2'-arabino modification is 2'-F. Similar modifications may also be made at other positions on the oligonucleotide, for example, at the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. See, for example, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, the disclosures of which are incorporated by reference in their entireties herein.

In some aspects, a modification of the sugar includes Locked Nucleic Acids (LNAs) in which the 2'-hydroxyl group is linked to the 3' or 4' carbon atom of the sugar ring, thereby forming a bicyclic sugar moiety. The linkage is in certain aspects is a methylene (—CH$_2$—)$_n$ group bridging the 2' oxygen atom and the 4' carbon atom wherein n is 1 or 2. LNAs and preparation thereof are described in WO 98/39352 and WO 99/14226.

Modified nucleotides are described in EP 1 072 679 and WO 97/12896, the disclosures of which are incorporated herein by reference. Modified nucleobases include without limitation, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzox-azin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Additional nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, Angewandte Chemie, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing binding affinity and include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; 5,750,692 and 5,681,941, the disclosures of which are incorporated herein by reference.

Methods of making polynucleotides of a predetermined sequence are well-known. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both polyribonucleotides and polydeoxyribonucleotides (the well-known methods of synthesizing DNA are also useful for synthesizing RNA). Polyribonucleotides can also be prepared enzymatically. Non-naturally occurring nucleobases can be incorporated into the polynucleotide, as well. See, e.g., U.S. Pat. No. 7,223,833; Katz, J. Am. Chem. Soc., 74:2238 (1951); Yamane, et al., J. Am. Chem. Soc., 83:2599 (1961); Kosturko, et al., Biochemistry, 13:3949 (1974); Thomas, J. Am. Chem. Soc., 76:6032 (1954); Zhang, et al., J. Am. Chem. Soc., 127:74-75 (2005); and Zimmermann, et al., J. Am. Chem. Soc., 124:13684-13685 (2002).

In various aspects, an oligonucleotide of the disclosure, or a modified form thereof, is generally about 10 nucleotides to about 100 nucleotides in length. More specifically, an oligonucleotide of the disclosure is about 10 to about 90 nucleotides in length, about 10 to about 80 nucleotides in length, about 10 to about 70 nucleotides in length, about 10 to about 60 nucleotides in length, about 10 to about 50 nucleotides in length about 10 to about 45 nucleotides in length, about 10 to about 40 nucleotides in length, about 10 to about 35 nucleotides in length, about 10 to about 30 nucleotides in length, about 10 to about 25 nucleotides in length, about 10 to about 20 nucleotides in length, about 10 to about 15 nucleotides in length, and all oligonucleotides intermediate in length of the sizes specifically disclosed to the extent that the oligonucleotide is able to achieve the desired result. In further embodiments, an oligonucleotide of the disclosure is about 5 nucleotides to about 1000 nucleotides in length. In further embodiments, an oligonucleotide of the disclosure is about 5 to about 900 nucleotides in length, about 5 to about 800 nucleotides in length, about 5 to about 700 nucleotides in length, about 5 to about 600 nucleotides in length, about 5 to about 500 nucleotides in length about 5 to about 450 nucleotides in length, about 5 to about 400 nucleotides in length, about 5 to about 350 nucleotides in length, about 5 to about 300 nucleotides in length, about 5 to about 250 nucleotides in length, about 5 to about 200 nucleotides in length, about 5 to about 150 nucleotides in length, about 5 to about 100 nucleotides in length, about 5 to about 90 nucleotides in length, about 5 to about 80 nucleotides in length, about 5 to about 70 nucleotides in length, about 5 to about 60 nucleotides in length, about 5 to about 50 nucleotides in length, about 5 to about 40 nucleotides in length, about 5 to about 30 nucleotides in length, about 5 to about 20 nucleotides in length, about 5 to about 10 nucleotides in length, and all oligonucleotides intermediate in length of the sizes specifically disclosed to the extent that the oligonucleotide is able to achieve the desired result. Accordingly, in various embodiments, an oligonucleotide of the disclosure is or is at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or more nucleotides in length. In further embodiments, an oligonucleotide of the disclosure is less than 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 200, 300, 400, 500, 600, 700, 800, 900, 1000, or more nucleotides in length.

Spacers. In some aspects, an oligonucleotide is attached to a nanoparticle through a spacer. "Spacer" as used herein means a moiety that serves to increase distance between the nanoparticle and the oligonucleotide, or to increase distance between individual oligonucleotides when attached to the nanoparticle in multiple copies. Thus, spacers are contemplated being located between individual oligonucleotides in tandem, whether the oligonucleotides have the same sequence or have different sequences.

In some aspects, the spacer when present is an organic moiety. In some aspects, the spacer is a polymer, including but not limited to a water-soluble polymer, a nucleic acid, a polypeptide, an oligosaccharide, a carbohydrate, a lipid, an ethylglycol, or a combination thereof. In any of the aspects or embodiments of the disclosure, the spacer is an oligo (ethylene glycol)-based spacer. In various embodiments, an oligonucleotide comprises 1, 2, 3, 4, 5, or more spacer (e.g., Spacer-18 (hexaethyleneglycol)) moieties. In further embodiments, the spacer is an alkane-based spacer (e.g., C12). In some embodiments, the spacer is an oligonucleotide spacer (e.g., T5). An oligonucleotide spacer may have any sequence that does not interfere with the ability of the oligonucleotide to perform an intended function (e.g., inhibit gene expression). In certain aspects, the bases of the oligonucleotide spacer are all adenylic acids, all thymidylic acids, all cytidylic acids, all guanylic acids, all uridylic acids, or all some other modified base.

In various embodiments, the length of the spacer is or is equivalent to at least about 2 nucleotides, at least about 3 nucleotides, at least about 4 nucleotides, at least about 5 nucleotides, 5-10 nucleotides, 10 nucleotides, 20 nucleotides, 10-30 nucleotides, or even greater than 30 nucleotides.

Oligonucleotide attachment to a nanoparticle. Oligonucleotides contemplated for use in the methods include those attached (i.e., functionalized) to a nanoparticle core through any means (e.g., covalent or non-covalent attachment). In any of the aspects or embodiments of the disclosure, the one or more oligonucleotides is attached to the external surface of the nanoparticle core. Regardless of the means by which the oligonucleotide is attached to the nanoparticle, attachment in various aspects is effected through a 5' linkage, a 3' linkage, some type of internal linkage, or any combination of these attachments. In some embodiments, the oligonucleotide is covalently attached to a nanoparticle. In further embodiments, the oligonucleotide is non-covalently attached to a nanoparticle.

Methods of attachment are known to those of ordinary skill in the art and are described in U.S. Publication No. 2009/0209629, which is incorporated by reference herein in its entirety. Methods of attaching RNA to a nanoparticle are generally described in PCT/US2009/65822, which is incorporated by reference herein in its entirety. Methods of associating oligonucleotides with a liposomal particle are described in PCT/US2014/068429, which is incorporated by reference herein in its entirety.

Nanoparticle surface density. A surface density adequate to make the nanoparticles stable and the conditions necessary to obtain it for a desired combination of nanoparticles and oligonucleotides can be determined empirically. Generally, a surface density of at least about 2 pmoles/cm$^2$ will be adequate to provide stable nanoparticle-oligonucleotide compositions. In some aspects, the surface density is at least 15 pmoles/cm$^2$. Methods are also provided wherein the oligonucleotide is bound to the nanoparticle at a surface density of at least 2 pmol/cm$^2$, at least 3 pmol/cm$^2$, at least 4 pmol/cm$^2$, at least 5 pmol/cm$^2$, at least 6 pmol/cm$^2$, at least 7 pmol/cm$^2$, at least 8 pmol/cm$^2$, at least 9 pmol/cm$^2$, at least 10 pmol/cm$^2$, at least about 15 pmol/cm2, at least about 19 pmol/cm$^2$, at least about 20 pmol/cm$^2$, at least about 25 pmol/cm$^2$, at least about 30 pmol/cm$^2$, at least about 35 pmol/cm$^2$, at least about 40 pmol/cm$^2$, at least about 45 pmol/cm$^2$, at least about 50 pmol/cm$^2$, at least about 55 pmol/cm$^2$, at least about 60 pmol/cm$^2$, at least about 65 pmol/cm$^2$, at least about 70 pmol/cm$^2$, at least about 75 pmol/cm$^2$, at least about 80 pmol/cm$^2$, at least about 85 pmol/cm$^2$, at least about 90 pmol/cm$^2$, at least about 95 pmol/cm$^2$, at least about 100 pmol/cm$^2$, at least about 125 pmol/cm$^2$, at least about 150 pmol/cm$^2$, at least about 175 pmol/cm$^2$, at least about 200 pmol/cm$^2$, at least about 250 pmol/cm$^2$, at least about 300 pmol/cm$^2$, at least about 350 pmol/cm$^2$, at least about 400 pmol/cm$^2$, at least about 450 pmol/cm$^2$, at least about 500 pmol/cm$^2$, at least about 550 pmol/cm$^2$, at least about 600 pmol/cm$^2$, at least about 650 pmol/cm$^2$, at least about 700 pmol/cm$^2$, at least about 750 pmol/cm$^2$, at least about 800 pmol/cm$^2$, at least about 850 pmol/cm$^2$, at least about 900 pmol/cm$^2$, at least about 950 pmol/cm$^2$, at least about 1000 pmol/cm$^2$ or more.

Alternatively, the density of oligonucleotide attached to the SNA is measured by the number of oligonucleotides attached to the SNA. With respect to the surface density of oligonucleotides attached to an SNA of the disclosure, it is contemplated that a SNA as described herein comprises about 1 to about 2,500, or about 1 to about 500 oligonucleotides on its surface. In various embodiments, a SNA comprises about 10 to about 500, or about 10 to about 300, or about 10 to about 200, or about 10 to about 190, or about 10 to about 180, or about 10 to about 170, or about 10 to about 160, or about 10 to about 150, or about 10 to about 140, or about 10 to about 130, or about 10 to about 120, or about 10 to about 110, or about 10 to about 100, or 10 to about 90, or about 10 to about 80, or about 10 to about 70, or about 10 to about 60, or about 10 to about 50, or about 10 to about 40, or about 10 to about 30, or about 10 to about 20 oligonucleotides in the shell of oligonucleotides attached to the nanoparticle core. In some embodiments, a SNA comprises about 80 to about 140 oligonucleotides in the shell of oligonucleotides attached to the nanoparticle core. In further embodiments, a SNA comprises at least about 5, 10, 20, 30, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 oligonucleotides in the shell of oligonucleotides attached to the nanoparticle core. In further embodiments, a SNA consists of 5, 10, 20, 30, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200 oligonucleotides in the shell of oligonucleotides attached to the nanoparticle core. In still further embodiments, the shell of oligonucleotides attached to the nanoparticle core of the SNA comprises 2, 3, 4, 5, 6, 7, 8, 9, 10, 11, 12, 13, 14, 15, 16, 17, 18, 19, 20 or more oligonucleotides. In some embodiments, the shell of oligonucleotides attached to the nanoparticle core of the SNA comprises at least 20 oligonucleotides. In some embodiments, the shell of oligonucleotides attached to the nanoparticle core of the SNA consists of 2, 3, 4, 5, 6, 7, 8, 9, 10, 11, 12, 13, 14, 15, 16, 17, 18, 19, or 20 oligonucleotides.

Uses of SNAs in Gene Regulation/Therapy

As disclosed herein, it is contemplated that in any of the aspects or embodiments of the disclosure, a SNA as disclosed herein possesses the ability to regulate gene expression. Thus, in some embodiments, a SNA of the disclosure comprises an oligonucleotide having gene regulatory activity (e.g., inhibition of target gene expression or target cell recognition). Accordingly, in some embodiments the disclosure provides methods for inhibiting gene product expression, and such methods include those wherein expression of a target gene product is inhibited by about or at least about 5%, about or at least about 10%, about or at least about 15%, about or at least about 20%, about or at least about 25%, about or at least about 30%, about or at least about 35%, about or at least about 40%, about or at least about 45%, about or at least about 50%, about or at least about 55%, about or at least about 60%, about or at least about 65%, about or at least about 70%, about or at least about 75%, about or at least about 80%, about or at least about 85%, about or at least about 90%, about or at least about 95%, about or at least about 96%, about or at least about 97%, about or at least about 98%, about or at least about 99%, or 100% compared to gene product expression in the absence of a SNA. In other words, methods provided embrace those which results in essentially any degree of inhibition of expression of a target gene product.

The degree of inhibition is determined in vivo from a body fluid sample or from a biopsy sample or by imaging techniques well known in the art. Alternatively, the degree of inhibition is determined in a cell culture assay, generally as a predictable measure of a degree of inhibition that can be expected in vivo resulting from use of a specific type of SNA and a specific oligonucleotide.

In various aspects, the methods include use of an oligonucleotide which is 100% complementary to the target polynucleotide, i.e., a perfect match, while in other aspects, the oligonucleotide is about or at least (meaning greater than or equal to) about 95% complementary to the polynucleotide over the length of the oligonucleotide, about or at least about 90%, about or at least about 85%, about or at least about 80%, about or at least about 75%, about or at least about 70%, about or at least about 65%, about or at least about 60%, about or at least about 55%, about or at least about 50%, about or at least about 45%, about or at least about 40%, about or at least about 35%, about or at least about 30%, about or at least about 25%, about or at least about 20% complementary to the polynucleotide over the length of the oligonucleotide to the extent that the oligonucleotide is able to achieve the desired degree of inhibition of a target gene product. Moreover, an oligonucleotide may hybridize over one or more segments such that intervening or adjacent segments are not involved in the hybridization event (e.g., a loop structure or hairpin structure). The percent complementarity is determined over the length of the oligonucleotide. For example, given an inhibitory oligonucleotide in which 18 of 20 nucleotides of the inhibitory oligonucleotide are complementary to a 20-nucleotide region in a target polynucleotide of 100 nucleotides total length, the oligonucleotide would be 90 percent complementary. In this example, the remaining noncomplementary nucleotides may be clustered or interspersed with complementary nucleobases and need not be contiguous to each other or to complementary nucleotides. Percent complementarity of an inhibitory oligonucleotide with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Accordingly, methods of utilizing a SNA of the disclosure in gene regulation therapy are provided herein. In various aspects, the method comprises the step of hybridizing a polynucleotide encoding the gene with an oligonucleotide that is attached to the surface of a SNA of the disclosure, wherein hybridizing between the polynucleotide and the oligonucleotide occurs over a length of the polynucleotide with a degree of complementarity sufficient to inhibit expression of the gene product. The inhibition of gene expression may occur in vivo or in vitro.

The oligonucleotide utilized in the methods of the disclosure is either RNA or DNA. The RNA can be an inhibitory RNA (RNAi) that performs a regulatory function, and in various embodiments is selected from the group consisting of a small interfering RNA (siRNA), a short hairpin RNA (shRNA), an RNA that forms a triplex with double stranded DNA, and a ribozyme. Alternatively, the RNA is microRNA that performs a regulatory function. The DNA is, in some embodiments, an antisense-DNA or a DNAzyme. The oligonucleotide is, in further embodiments, an aptamer or an aptazyme.

Uses of SNAs in Immune Regulation

Toll-like receptors (TLRs) are a class of proteins, expressed in sentinel cells, that play a key role in regulation of innate immune system. The mammalian immune system uses two general strategies to combat infectious diseases. Pathogen exposure rapidly triggers an innate immune response that is characterized by the production of immunostimulatory cytokines, chemokines and polyreactive IgM antibodies. The innate immune system is activated by exposure to Pathogen Associated Molecular Patterns (PAMPs) that are expressed by a diverse group of infectious microorganisms. The recognition of PAMPs is mediated by members of the Toll-like family of receptors. TLR receptors, such as TLR 4, TLR 8 and TLR 9 that respond to specific oligonucleotide are located inside special intracellular compartments, called endosomes. The mechanism of modulation of, for example and without limitation, TLR 4, TLR 8 and TLR 9 receptors, is based on DNA-protein interactions.

Synthetic immunostimulatory oligonucleotides that contain CpG motifs that are similar to those found in bacterial DNA stimulate a similar response of the TLR receptors. Therefore, immunomodulatory oligonucleotides have various potential therapeutic uses, including treatment of immune deficiency and cancer. Thus, in some embodiments, a SNA of the disclosure comprises an oligonucleotide that is a TLR agonist. In some embodiments, the immunostimulatory oligonucleotide is a double-stranded DNA (dsDNA) that can activate a stimulator of interferon (STING) gene.

In further embodiments, down regulation of the immune system would involve knocking down the gene responsible for the expression of the Toll-like receptor. This antisense approach involves use of a SNA of the disclosure to knock down the expression of any toll-like protein.

Accordingly, in some embodiments, methods of utilizing SNAs as described herein for modulating toll-like receptors are disclosed. The method either up-regulates or down-regulates the Toll-like-receptor activity through the use of a TLR agonist or a TLR antagonist, respectively. The method comprises contacting a cell having a toll-like receptor with a SNA of the disclosure, thereby modulating the activity and/or the expression of the toll-like receptor. The toll-like receptors modulated include one or more of toll-like receptor 1, toll-like receptor 2, toll-like receptor 3, toll-like receptor 4, toll-like receptor 5, toll-like receptor 6, toll-like receptor 7, toll-like receptor 8, toll-like receptor 9, toll-like receptor 10, toll-like receptor 11, toll-like receptor 12, and/or toll-like receptor 13.

EXAMPLES

Aspects of the disclosure provide a universal method for targeting SNAs to specific cell types. To accomplish this goal, SNAs were designed and synthesized with predefined protein coronae consisting of specific functional proteins electrostatically immobilized on the oligonucleotide shell. The stability of these structures was then explored in buffer and human serum. In addition, their ability to hybridize with complementary oligonucleotides, as well as selectively target cell populations based on molecular signatures present on the cell surface, was studied. For example, SNAs with adsorbed human epithelial growth factor receptor 2 (HER2) monoclonal antibodies (mAb) exhibited selectivity for HER2-positive breast cancer cells in mixed cell cultures with HER2-negative breast cancer cells. Taken together, the examples demonstrate an easy, efficient, and flexible method for controlling SNA interactions within cells that has the potential to vastly improve SNA stability, cell targeting, and biodistribution.

The following examples demonstrate that SNAs with adsorbed targeting antibodies exhibited improved cellular selectivity within mixed cell populations. Similarly, SNAs coated with the dysopsonizing protein, serum albumin, showed reduced macrophage uptake, providing a strategy for tailoring selective SNA delivery. Importantly, these SNAs with designed coronae remained stable in human serum, exhibiting less than 45% loss of protein through exchange after 12 h at 37° C. Taken together, these structures and the method used to prepare them provide new avenues for enhancing SNA stability, targeting, and biodistribution.

Example 1

Particle synthesis and characterization. In order to generate particles with defined protein coronae, native SNAs were first synthesized by functionalizing 13-nm gold nanoparticles (AuNPs) with thiolated oligodeoxynucleotides (ODNs) using established freezing directed synthetic methods.[42] These SNAs were then incubated with different functional proteins, such as human epithelial growth factor receptor 2 monoclonal antibodies (anti-HER2), immunoglobulin G (IgG), and human serum albumin (HSA). Each protein was selected based upon its potential ability to confer specific targeting properties to SNAs. Specifically, anti-HER2 was used as a model protein for cell targeting because it is a clinically relevant target for HER2-positive breast cancer.[43] IgG was used because it is an immunogenic protein that attracts macrophages, while HSA was explored because it can shield nanoparticles from liver clearance and macrophage uptake.[44] After incubating the individual proteins with the SNAs, the loosely bound proteins were washed away by pelleting the particles via centrifugation, leaving primarily a hard corona, known to bind to NP surfaces with higher affinity, adsorbed onto the SNA surface.[45]

Figure 2:
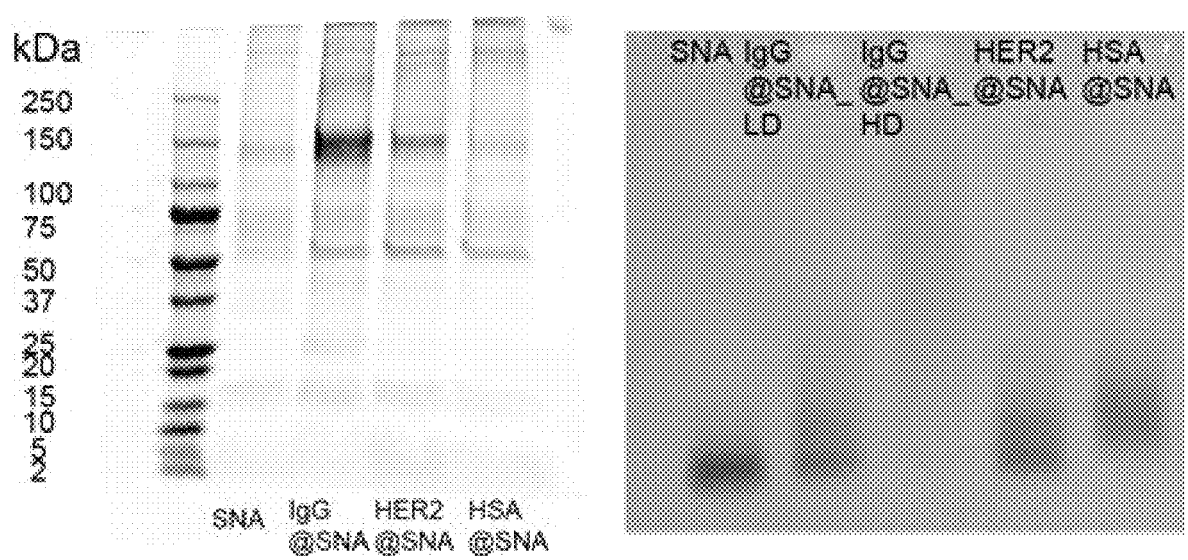
FIG. 2 shows a gel electrophoresis analysis of the protein-adsorbed SNAs and their extracted hard protein corona. (A) Protean TGX gel electrophoresis of the protein standards (lane 1), SNAs (lane 2), IgG-adsorbed SNAs (lane 3), anti-HER2-adsorbed SNAs (lane 4), and HSA-adsorbed SNAs (lane 5). (B) 1% agarose gel electrophoresis of SNAs (lane 1), low-density IgG-adsorbed SNAs (lane 2), high-density IgG-adsorbed SNAs (lane 3), anti-HER2-adsorbed SNAs (lane 4), and HSA-adsorbed SNAs (lane 5).

To verify the formation of a hard corona, the diameter and zeta-potential ($\zeta$-potential) of the SNAs were measured before and after incubation with the different proteins (FIG. 1). Dynamic light scattering (DLS) revealed that the average diameter of IgG-adsorbed SNAs (28.3±4.1 nm), anti-HER2-adsorbed SNAs (23.5±2.1 nm), and HSA-adsorbed SNAs (19.6±1.4 nm) was larger than the non-coated SNAs (15.1±2.2 nm). Furthermore, the IgG (−28.0±0.6 mV) and HSA (−24.0±3.6 mV) adsorbed SNAs displayed a more positive $\zeta$-potential when compared to non-coated SNAs (−35.4±2.4 mV). As further verification of protein corona formation, the electrophoretic mobility of SNAs was examined after incubation with proteins. All SNAs with protein coronae had reduced mobility in an agarose gel, compared to unmodified SNAs (FIG. 2), further confirming that protein adsorption occurred.

Stability of protein coronae in biological fluids. After establishing that an initial protein corona could be adsorbed on the SNAs, the stability of the protein corona was examined by studying the exchange dynamics of proteins on the surface of SNAs in serum-rich conditions (i.e., 10% human serum (HS)). To accomplish this objective, SNAs were synthesized with Cy5-labeled ODNs, to which proteins labeled with Texas Red-X were adsorbed, a fluorophore that can transfer emitted energy to the Cy5 fluorophore on the ODN shell when attached to the SNAs. Thus, as proteins were displaced from the particle surface, an increase in Texas Red-X was observed. The SNAs were incubated in 10% HS at 37° C. and the change in fluorescence tracked for 12 h, at which point the change in fluorescence had slowed significantly (FIG. 1E). After 12 h, it was found that more than 55% of the initial corona remained, indicating a stable hard protein corona had formed on the SNAs. Compared to IgG and anti-HER2, adsorbed HSA tended to dissociate from the SNA surface, even without serum, indicating its weaker affinity for the ODN shell; the addition of serum increases the HSA desorption slightly. Significantly, the stable adhesion of the functional proteins ensured that active protein coronae is retained even in physiologically relevant media.

Oligonucleotide properties with pre-adsorbed protein coronae. The characteristics of SNAs pre-coated with corona proteins were explored to ensure that they retained some of the same key biological properties of the original SNAs that make them valuable in biology and medicine. First, their resistance to nucleases was examined by quantifying the amount of ODNs degraded. To measure degradation, SNAs were synthesized with Cy5-labeled ODNs; the Cy5 in this structure was quenched when attached to the gold core. Upon incubation with deoxyribonuclease I (DNase I), an endonuclease, ODNs are cleaved from the AuNP core, resulting in increased Cy5 emission intensity. In this experiment, pre-adsorption of IgG or HSA significantly reduced both the rate and efficiency of ODN degradation, and anti-HER2 coating lessened the ODN degradation efficiency, compared to the SNAs without a protein corona (FIG. 3B); this result indicated that pre-adsorption of proteins enhanced SNA resistance to nucleases. Without wishing to be bound by theory, this presumably occurred due to the increased steric hindrance of the protein corona that prevented nucleases from accessing the ODNs.

Figure 3:
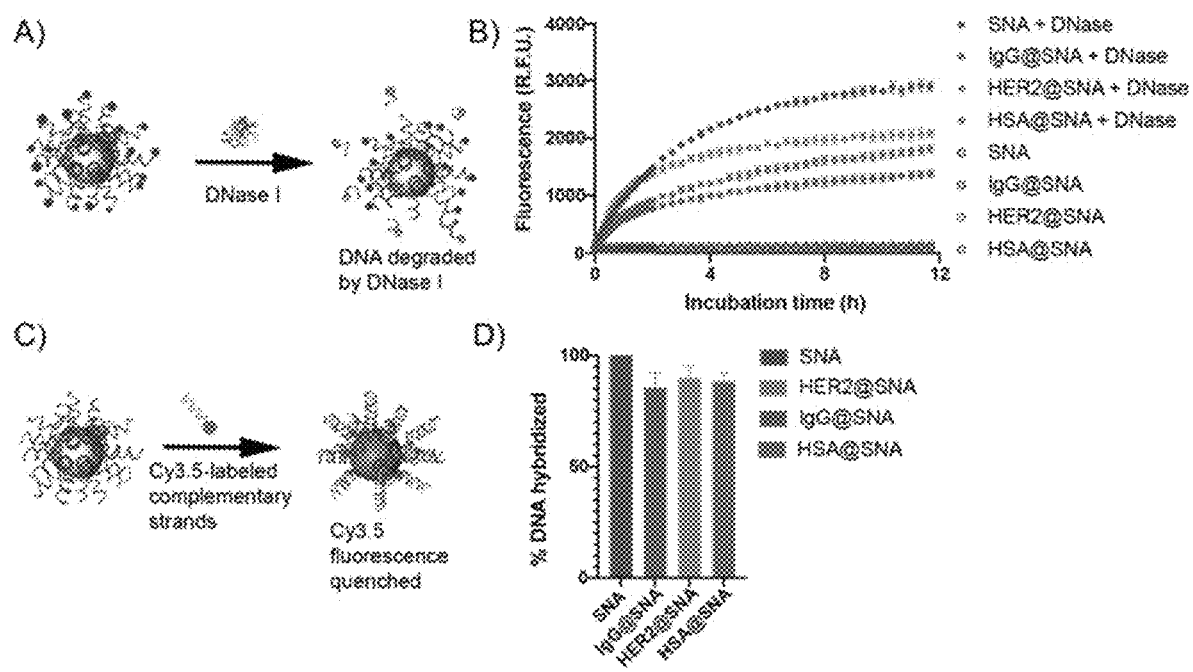
FIG. 3 shows the in vitro properties of SNAs pre-adsorbed with functional proteins. (A) Schematic representation of the degradation of the ODN shell in the presence of DNase I, in which the Cy5 fluorophore attached to the outer shell is no longer quenched by AuNPs following protease degradation. (B) The fluorescence kinetic profile of the SNAs, IgG-immobilized SNAs and HSA-immobilized SNAs with and without DNase I treatment. (C) Schematic representation of the hybridization of Cy3.5-labeled complementary strands to the ODNs immobilized on AuNPs. Fluorescence is quenched as hybridization occurs. (D) The degree of hybridization of SNAs with complementary strands on anti-HER2-adsorbed SNAs, IgG-adsorbed SNAs, and HSA-adsorbed SNAs, relative to that of SNAs without a protein corona.

Given that the ODNs are potentially sterically hindered when a protein corona is adsorbed to the structures, it was examined whether the protein corona reduced their ability to recognize complementary binding partners, a necessary step for antisense and RNA interference pathways as well as mRNA sensing. To assess this property, an AuNP-based fluorescence quenching assay was designed, in which the hybridization of fluorescently labeled (i.e., Cy3.5) strands complementary to those making up the SNA shell results in quenching, due to the proximity of Cy3.5 fluorophore to the AuNP cores. The quenching of the Cy3.5 fluorescence by AuNP core is an indicator of the amount of hybridization, and therefore was a measure of the surface DNA accessibility (FIG. 3C). Surprisingly, it was found that the pre-adsorbed protein corona only decreased DNA accessibility by approximately 10% (FIG. 3D) compared to native SNAs, implying that SNAs could still be functional in nucleic acid therapeutic schemes.

Figure 4:
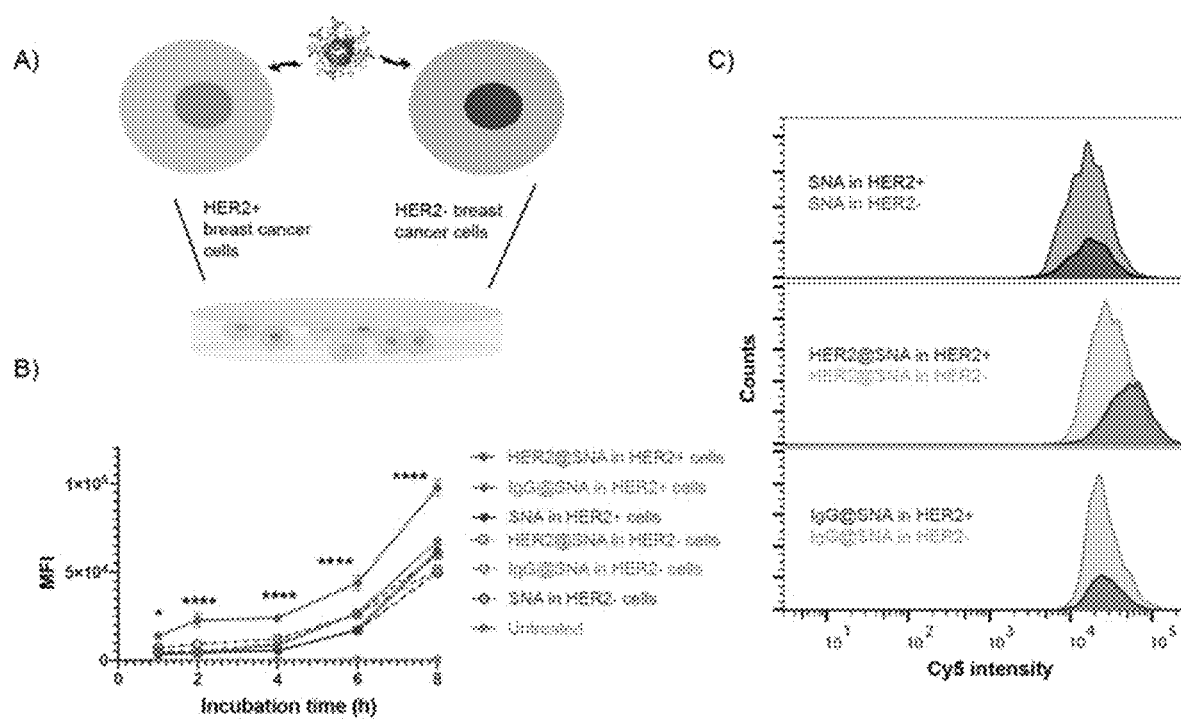
FIG. 4 shows the selective cellular uptake of the monoclonal HER2 antibody-adsorbed SNAs. (A) Schematics of the SNA treatment of the co-cultured HER2-expressing breast cancer cells, SK-BR-3, and non-HER2-expressing breast cancer cells, MDA-MB-231. (B) Uptake profile of anti-HER2-adsorbed SNAs, IgG-adsorbed SNAs, and SNAs following 1-8 h incubation with the co-cultured cells (filled circle: HER2-positive cells; hollow circles: HER2-negative cells). (C) The overlaid histograms of the co-cultured breast cancer cells by Cy5 intensity after treated with anti-HER2-adsorbed SNA, IgG-adsorbed SNAs, and SNAs for 6 h. The distribution of Cy5 fluorescence of HER2+ cells is in darker shades and that of the HER2-cells is in lighter shades.

Cellular selectivity of the antibody-immobilized SNAs. On a cellular level, it was investigated whether pre-adsorbed protein coronae on SNAs could be used to modulate their uptake by targeted cell types. A key attribute of SNAs is that they enter nearly any cell type (over 50 to date),[24] an especially powerful property for many therapeutic and diagnostic applications; notably, selective targeting could impart an enhanced therapeutic effect. As a first test, the targeting capabilities of antibody-immobilized SNAs was examined. For these experiments, SNAs were synthesized with an ODN shell containing 10% Cy5-labeled strands for flow cytometry detection, thereby minimizing potential perturbation to the uptake pathway caused by the fluorophore. These constructs were then incubated with either anti-HER2 mAbs or a non-targeting antibody, IgG. The selectivity of the SNAs was assessed by treating co-cultured breast cancer cells lines, SK-BR-3 (HER2 overexpressing) and MDA-MB-231 (HER2 negative) with the particles (FIG. 4A). Furthermore, the MDA-MB-231 cells were engineered to express green fluorescent protein (GFP), such that the two cell lines can be separated based on fluorescence intensity by flow cytometry (FIG. 4B). Significantly, only the anti-HER2-adsorbed SNAs preferentially entered the HER2-positive cells compared to HER2-negative ones across an 8 h treatment time. In contrast, non-targeting IgG-adsorbed SNAs and native SNAs showed no cellular selectivity. Importantly, pre-coating SNAs with non-targeting proteins did not seem to reduce their cancer cell uptake efficiency, compared to that of the SNAs (FIG. 4C). This finding was consistent with a previous report that mAb functionalization improves cellular selectivity,[17] but the physical adsorption of mAb demonstrated here was easier and more adaptable than the reported conjugation approach. Significantly, cells were treated with mAb-adsorbed SNAs in complete growth media supplemented with 10% serum, and the targeting capabilities still persisted. These conditions showed that mAb-adsorbed SNAs were able to retain the cellular selectivity even in the presence of other serum proteins.

Figure 5:
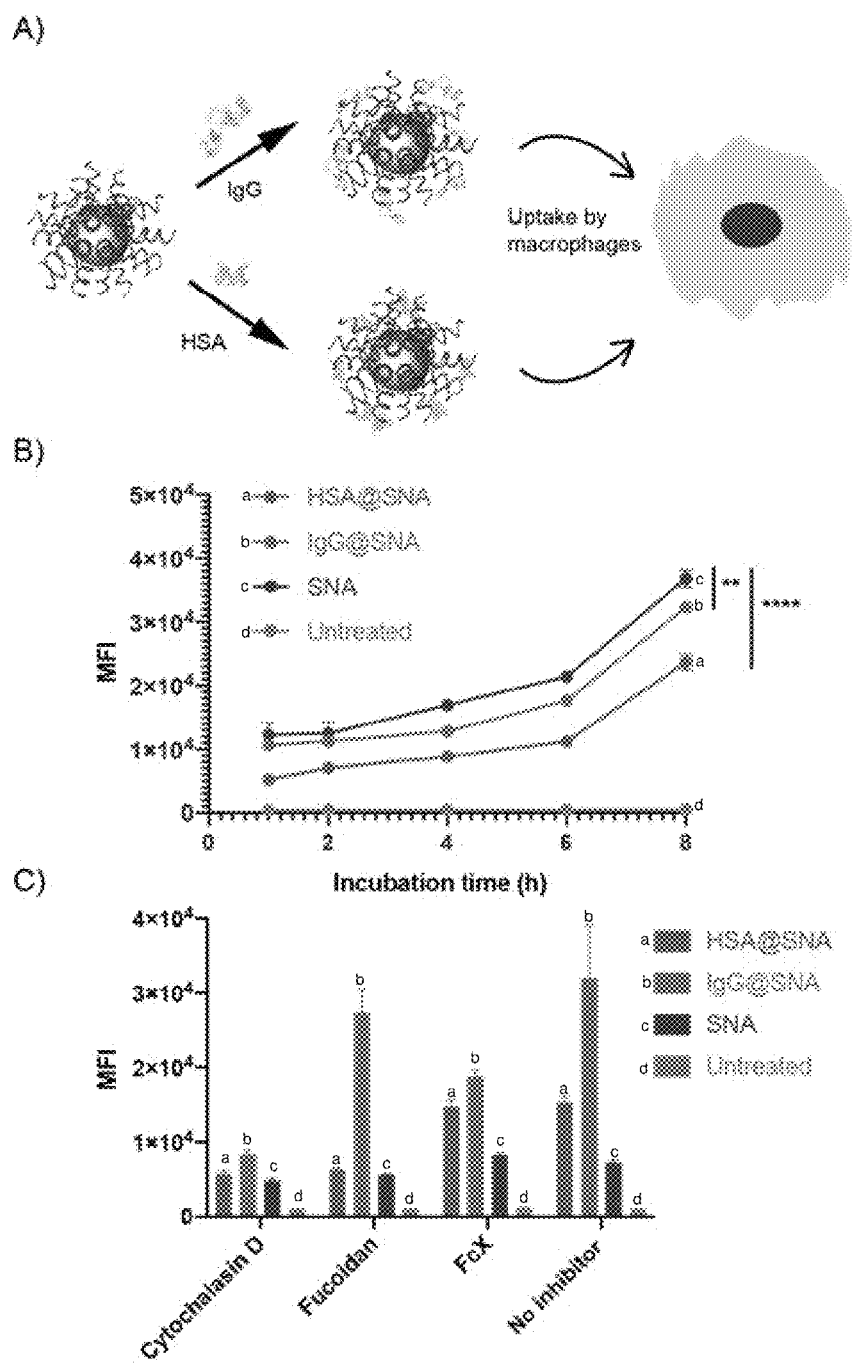
FIG. 5 demonstrates the cellular uptake of the IgG (opsonin) and HSA (dysopsonin)-adsorbed SNAs. (A) Schematics of the SNA treatment of THP-1-derived macrophages. (B) Uptake of HSA-adsorbed SNAs, IgG-adsorbed SNAs, and SNAs following 1-8 h incubation with THP-1-derived macrophages. (C) Receptor inhibited THP-1 macrophage uptake of HSA-adsorbed SNAs, IgG-adsorbed SNAs, and SNAs following pre-treatment of cytochalasin D, fucoidan, or Fc receptor blocker (FcX).
Figure 6:
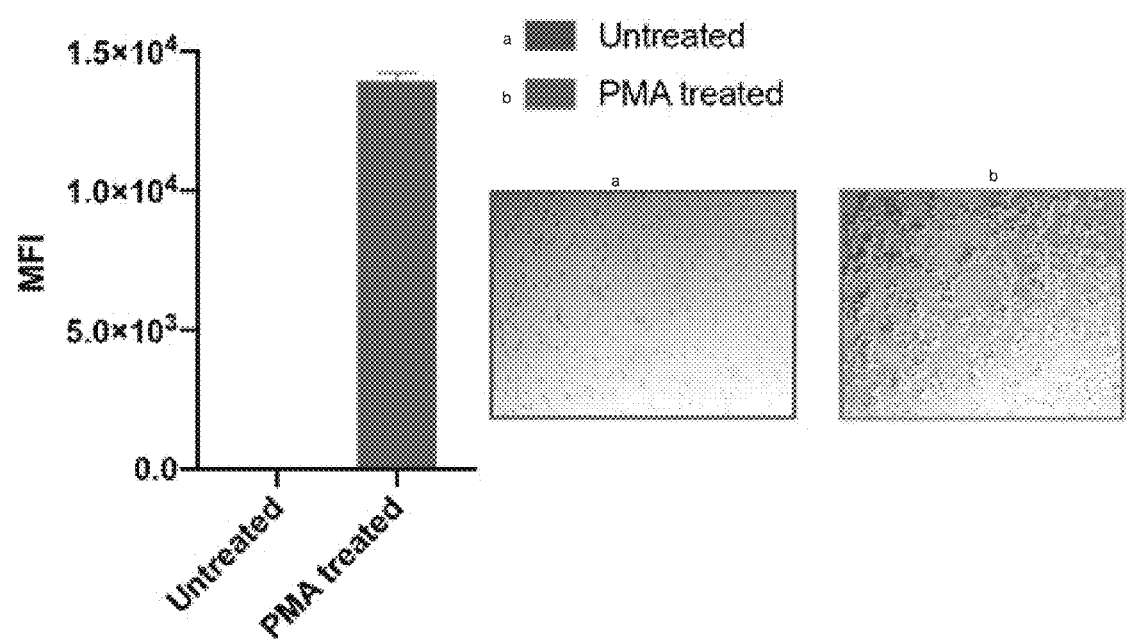
FIG. 6 shows the change of expression level of a surface marker, CD14 of THP-1 before (blue) and after (red) PMA treatment. Insert: change of morphology followed by PMA differentiation.

Evasion of macrophage clearance of the dysopsonin-adsorbed SNAs. Lastly, the potential use of the approach described herein to create SNAs that can target or avoid macrophages, which play central roles in immunomodulation and clearance, was investigated. For this purpose, either a recognized opsonin, IgG,[46] or a dysopsonin, HSA,[18] was pre-adsorbed on the ODN shell of SNAs and incubated with human macrophages (FIG. 5A). Typically, an opsonin marks a construct as foreign and induces macrophage clearance, while dysopsonin does the opposite. To perform this experiment, human monocytes THP-1 were first differentiated into macrophages using phorbol 12-myristate-13-acetate (PMA; FIG. 6).[47-48] The macrophages were then treated with native and active protein-coated SNAs for 1-8 h at 37° C. It was hypothesized that IgG pre-adsorption would improve SNA uptake efficiency by macrophages, while HSA pre-adsorption would reduce it.[18, 49] Interestingly, both IgG and HSA adsorption lowered the uptake of the SNAs into the macrophages with HSA adsorption having a more significant impact on reducing SNA clearance by macrophages (FIG. 5B). IgG is an opsonin that can be cleared by macrophages through Fc receptor recognition,[50] while non-protein coated SNAs and HSA alone are reported to enter cells through scavenger receptor A (SR-A) recognition.[51-52] It was speculated that coating SNAs with IgG would alter their uptake pathways, and indeed, significantly diminished uptake efficiency was observed for these SNAs when the Fc receptors were blocked by FcX (FIG. 5C). As a comparison, when SR-A was inhibited by fucoidan, the reduction in uptake efficiency of non-coated SNAs and HSA-immobilized SNAs was more significant than that of the IgG-adsorbed SNAs. Since macrophages are phagocytic, when phagocytosis was inhibited by cytochalasin D, the uptake of all of the SNA types was suppressed. Taken together, these results indicated that IgG-immobilization alters the major cellular uptake pathway of SNAs, which could be the reason for the overall reduction of uptake efficiency. Significantly, the HSA coating of SNAs reduced nonspecific macrophage uptake compared to native SNAs, opening new avenues to explore for increasing blood circulation half-life.

In summary, the experiments described herein demonstrated an easy and flexible method of incorporating active protein coronae on SNA surface at a relatively high stability even in the presence of serum. Significantly, this method imparted cellular selectivity to SNAs and reduces nonspecific macrophage clearance, without interfering with the performance of the oligonucleotide shell. This methodology, depending upon surface characteristics, can be generally applied to other nanomaterials to improve cellular selectivity. This work pointed towards strategies for improving SNA targeting and distribution in vivo, which impacts therapeutic development.

Materials. All materials were purchased from Sigma-Aldrich Co., MO, USA, and used without further purification or modification unless otherwise stated. All cell culture reagents were purchased from ThermoFisher Scientific, MA, USA. Human ErbB2 mAb was purchased from R&D Systems, MN, USA (accession number P04626).

Oligonucleotide synthesis and purification. The oligonucleotides for this study were synthesized on a solid support using a MerMade 12 automated DNA synthesizer (MM12, BioAutomation, TX, USA) using standard protocols. Reagents were purchased from Glen Research (VA, USA). After synthesis, the oligonucleotides were cleaved off from the solid support via addition of concentrated ammonium hydroxide (28-33% in water). Deprotection was carried out in ammonium hydroxide for 16 h at room temperature, after which ammonia was removed from the solution by purging with nitrogen for three hours at room temperature. The oligonucleotides were separated from the solid support by syringe filtration through a 0.22 μm filter. The resulting oligonucleotide solution was purified using reverse-phase high-performance liquid chromatography (RP-HPLC; Agilent, CA, USA) using a water/3% acetonitrile/3% triethylammonium acetate (A)-acetonitrile (B) solvent system. Label-free oligonucleotides were purified on a C18 column (250 mm×10 mm, Microsorb 300 Å/10 μm) using a gradient from 0-75% solvent B in 40 minutes at 3 mL/min. Fluorophore-labeled sequences were purified on a C4 column, using the same gradient and flow rate. Peaks corresponding to the product were manually collected and lyophilized for 1-2 days to fully remove the solvent. The dried products were dissolved in a 20% acetic acid solution to remove the trityl protecting groups for 1 h at room temperature. The protecting group was then extracted with ethyl acetate three times prior to collecting and lyophilizing the aqueous layer. The final product was dissolved in water and characterized by mass-to-charge ratio using MALDI-ToF-MS (AutoFlex-III, Bruker, MA, USA) in linear negative mode in the presence of dihydroxyacetone phosphate (DHAP) matrix.

Oligonucleotides (300-fold excess) were then functionalized onto AuNPs through freezing directed synthesis.[42] For the SNAs used in cellular uptake studies, 10% of thiolated Cy5-T20 strands, along with the thiolated label-free control 1826 ODN, were initially functionalized onto AuNPs. To ensure equivalent structures, SNAs made in the same batch were used in all experiments. Unbound oligonucleotides were removed via spin filtration (50 k Da MWCO; 4,000 rpm for 10 minutes). The eluent was discarded, and the +particles were washed with Dulbecco's phosphate buffered saline (DPBS) containing 0.01% Tween 20, and then they were centrifuged, and the filtrate was discarded. After repeating the wash step three times, the particles were resuspended in PBS, and the SNA concentration was measured using UV-vis spectroscopy as described above. To determine the oligonucleotide loading density on the AuNPs, known concentrations of SNAs were treated with 0.1 M KCN to dissolve the AuNP core. Oligonucleotide concentration was then determined by measuring the ODN absorbance at 260 nm. The average number of oligonucleotides functionalized on a nanoparticle was calculated by dividing the concentration of oligonucleotides by that of nanoparticles. The SNA solution was stored at 4° C. in the dark.

Protein labeling. To study the desorption kinetics of adsorbed proteins, human immunoglobulin G (IgG), human anti-HER2 antibody (anti-HER2), human serum albumin (HSA) (Sigma-Aldrich, MO, USA) were labeled with Texas Red-X succinimidyl ester, mixed isomers (ThermoFisher, MA, USA) following the manufacturer's protocol. The labeling was found to be 2.8, 2.9 and 1.7 of Texas Red-X fluorophores per IgG, anti-HER2, and HSA, respectively.

Adsorption of Proteins on SNAs. To adsorb functional proteins on the surface of SNAs, 1 mL of a 10 nM SNA solution was prepared in 2-(N-morpholino) ethanesulfonic

TABLE 1

Oligonucleotide sequences used in the studies described herein.

| NAME OF STRAND | APPLICATION | SEQUENCE | SEQ ID NO: |
|---|---|---|---|
| 1826 Control | AuNP functionalization | 5'-TCC ATG AGC TTC CTG AGC TT-(SP18)$_2$-SH-3' | 1 |
| T20 | AuNP functionalization | 5'-TTT TTT TTT TTT TTT TTT TT-(SP18)$_2$-SH-3' | 2 |
| Complementary Scrambled | Hybridize to scrambled 1826 for DNA accessibility quantification | 5'-CY3.5-AAG CTC AGG AAG CTC ATG GA-3' | 3 |
| Cy5-T20 | AuNP functionalization and labeling | 5'-CY5-TTT TTT TTT TTT TTT TTT TT-(SP18)$_2$-SH-3' | 4 |
| 1826 | AuNP functionalization and raw blue cell stimulation | 5'-TCC ATG ACG TTC CTG ACG TT-(SP18)$_2$-SH-3' | 5 |

Gold nanoparticle synthesis and oligonucleotide functionalization. The protocol used for the synthesis of citrate-stabilized 13-nm gold nanoparticles (AuNPs) was adapted from the Frens method.[53] Following synthesis and purification, the concentration of AuNPs and oligonucleotides was determined using a Cary 5000 UV-vis (Agilent Technologies, CA, USA); the absorbance of AuNPs at 520 nm was recorded, and the concentration was calculated using Beer's Law with an extinction coefficient of $2.76 \times 10^8$ M$^{-1}$ cm$^{-1}$.[54] For oligonucleotides, the absorption at 260 nm was recorded, and the extinction coefficient was obtained for each sequence using the IDT Oligo Analyzer (IL, USA).

acid (MES) buffer (pH 6.0, BioWorld, TX, USA). The SNA solution was then slowly added to 1 mL of protein solution (20-fold excess of HER2 mAb and IgG, 200-fold excess of HSA and IgG) in MES buffer while stirring. The mixture was incubated for 4 h at room temperature with constant stirring. The product was pelleted by centrifugation for 1 h at 15,300×g at 4° C., and the supernatant was removed.[55] The pellet was then washed with PBS twice at the same centrifugation setting. The protein-adsorbed SNA pellet was then suspended in approximately 100 μL of PBS, and the AuNP content was determined by absorbance using UV-vis spectroscopy.

DNA degradation assay. To quantify the amount of oligonucleotides degraded by DNase I on SNAs with and without the functional protein corona, a degradation assay was performed. Texas Red X-labeled IgG, anti-HER2, and HSA were immobilized on SNAs functionalized with 100% Cy5-labeled oligonucleotides. In a black 96-well plate, IgG-SNA, anti-HER2 SNA, HSA-SNA, or SNA (100 pmol by ODN) was diluted in 1× DNase I reaction buffer and mixed with 1 μL of DNase I (New England BioLabs, MA, USA) to make a final volume of 100 μL. The fluorescence was monitored on a plate reader (Cytation 5, BioTek Instruments, VT, USA) at 650/672 nm (10 nm slit width) at 37° C., over 12 h at 5 min intervals for the first two hours, and 20 min intervals thereafter.

Protein displacement assay in the presence of serum. The dissociation rate of pre-adsorbed functional proteins in the presence of serum is determined by a fluorescence-based assay. Texas Red X-labeled IgG, anti-HER2 and HSA were immobilized on SNAs functionalized with 100% Cy5-labeled oligonucleotides. As the protein coating leaves the Cy5-labeled oligonucleotide shell, the fluorescence of Texas Red X was restored. In a black 96-well plate, IgG@SNA, anti-HER2@SNA, HSA@SNA, or SNA was diluted in PBS supplemented with 10% HS to 5 nM by AuNP concentration. The fluorescence was monitored on a plate reader (Cytation 5, BioTek Instruments, VT, USA) at 595/616 nm (10 nm slit width) at 37° C., over 12 h at 5 min intervals for the first two hours, and 20 min intervals thereafter. A final reading was taken after addition of 1 μL of 10% SDS to each well to establish the full protein dissociation point.

On-particle DNA hybridization assay. The accessibility of the oligonucleotides on the SNA surface in the presence of protein corona was measured by a fluorescence-based DNA hybridization assay. In a black 96-well plate, SNA functionalized with label-free ODNs (500 nM final concentration by ODN) and its Cy3.5-labeled complementary strand (600 nM by final concentration) were combined in PBS. The mixture was incubated for 5 min at room temperature with constant shaking to allow for hybridization. The fluorescence intensity of Cy3.5 was measured on a Cytation 5 plate reader (excitation at 591 nm, emission at 611 nm, 9 nm slit width) at room temperature. The % DNA hybridized to protein-immobilized SNAs was calculated by assuming 100% hybridization for protein-free SNAs and 0% hybridization for SNAs functionalized with non-complementary (i.e., T20) strands.

Cell culture. Cells were cultured in a 5% $CO_2$ incubator following the suppliers' protocols. SK-BR-3 cells were cultured in McCoy 5A supplemented with 10% fetal bovine serum (FBS) and 1% penicillin/streptomycin (P/S). MDA-MB-231 GFP cells were cultured in DMEM containing 10% FBS, 1% P/S, 1× non-essential amino acids (NEAA) and 1× GlutaMAX. THP-1 macrophages were cultured in Rosewell Park Memorial Institute (RPMI) containing 10% FBS, 1% P/S, and 50 μM of 2-mercaptoethanol.

Antibody-adsorbed SNA uptake in breast cancer cells. To examine if ErbB2 mAb adsorption on SNAs can increase the uptake by cells overexpressing HER2, SK-BR-3 (HER2-positive) and MDA-MB-231 GFP (HER2-negative) cell lines were used. In a typical experiment, SK-BR-3 cells were plated in a 96-well plate at $1×10^4$ cells/well and MDA-MB-231 GFP were plated at $0.7×10^4$ cells/well in the same wells as SK-BR-3 cells. Both cells were plated in their corresponding complete growth media. The cells grew for at least 20 hours before being treated with SNAs. The cells were incubated with mAb-SNA, IgG-SNA, or SNAs (2 nM by AuNP, with 10% Cy5-labeled oligonucleotides) for 1, 2, 4, 6, 8 h, and the cells without treatment were used as blank control. After each time point, the cells were washed with PBS once and detached by adding 30 μL of TrypLE per well followed by incubation at 37° C. for 10 minutes. The cells were then fixed in a 3.7% paraformaldehyde (PFA) solution for 15 minutes at room temperature. 100 μL of PBS was added per well before flow cytometry analysis. Flow cytometry (LSRFortessa, BD Biosciences, CA, USA) measurements were conducted using the green and red laser; FITC and APC channels were selected for GFP and Cy5 detection, respectively. The distribution of cell fluorescence of the gated cells was collected. The two cell populations were separated based on FITC signal and the median fluorescence intensity (MFI) in the APC channel was calculated using FlowJo v10 (FlowJo LLC, OR, USA).

Opsonin-adsorbed SNA uptake in macrophages. To investigate if adsorption of opsonin (IgG) and a control protein (HSA) on SNAs can affect uptake by macrophages, THP-1 monocytes were first differentiated into macrophages. One million THP-1 cells were seeded in a 1.2 mL polystyrene test tube. Cells were then differentiated with 100 nM PMA in complete growth media for 72 h. On the fourth day, cells were pelleted (1,000 rpm, 5 min) and allowed to rest in PMA-free media for 24 h before SNA treatment. Differentiated THP-1 macrophages were then treated with 2 nM of IgG-SNA, HSA-SNA, or SNAs (labeled with 10% Cy5-oligonucleotides) for 1, 2, 4, 6, and 8 h; cells without treatment were used a blank control. After each time point, cells were pelleted (1,000 rpm, 5 min) and washed once with PBS. After that, cells were stained with LIVE/DEAD fixable violet dead cell stain kit (ThermoFisher) following the manufacturer's instructions. After washing with PBS twice, the cells were then fixed in 1 mL of 3.7% PFA solution for 15 minutes at room temperature, washed once with 1 mL of PBS with 1% bovine serum albumin (BSA). Cells were suspended in 0.15 mL of PBS with 1% BSA and analyzed by flow cytometry (LSRFortessa, BD Biosciences, CA, USA) in the APC channel for Cy5 signal quantification. The distribution of Cy5 fluorescence of the gated live cells (Pacific Blue channel) were collected and the corresponding MFI values were calculated using FlowJo v10.

Receptor inhibition studies. In 1.2 mL polystyrene test tubes, THP-1 macrophages were rested in full growth media for 5 days, before being suspended in 100 μL of media. Cells were pretreated with 50 μg/mL of fucoidan, 10 μM of cytochalasin D, or 5 μL of the FcX Fc receptor blocking solution (BioLegend, CA, USA) for 30 minutes at 37° C. before treatment with 5 nM (by AuNP) of 10% Cy5-labeled SNAs, and the cells were incubated for another 1 h at 37° C. To measure the extent of blocking, the cells were pelleted, fixed in 3.7% PFA (15 min, room temperature), and resuspended in 0.15 mL of PBS with 1% BSA for flow cytometry analysis in the APC channel for Cy5 signal quantification.

Protein-adsorbed SNA characterization. DLS measurements were taken on a Zetasizer NanoZS (Malvern Instruments, UK) using the refractive index of gold. Samples were prepared in water with a AuNP concentration of 1 nM. Measurements were conducted at 25° C. The diameter was reported for the number average of five measurements of each sample, and for zeta potential, the average of five measurements was reported. The protein-immobilized SNAs were also analyzed by 1% agarose gel in 1× TBE (Tris/borate/EDTA) buffer. The samples were loaded in the wells with 6× gel loading dye (10 uL of 20 nM [AuNP]/well; 2 uL loading dye/well; New England BioLabs, MA, USA). The chamber was filled with 300 mL of 1× TBE. The gel was run at 120 V for 1 h at r.t. and was imaged with Amersham Typhoon 5 Biomolecular Imager (GE Healthcare Life Sciences, PA, USA) in the densitometry mode.

Isolation of serum proteins on SNAs. IgG-SNA, HSA-SNA, and SNA (10 nM) were incubated in 10% type AB male human serum (HS) for 90 min at 37° C. with constant shaking. Unbound protein was then removed by centrifugation for 50 min at 153,000 rcf at 4° C. After removal of the supernatant, the pellet was washed with PBS twice. The SNA pellet was then resuspended in approximately 20 µL of 0.1% SDS. The mixture was heated for 5 min at 95° C. to dissociate the bound protein. The released protein was then separated from SNAs by centrifugation for 50 min at 153,000 rcf at 4° C., and the supernatant was collected for gel electrophoresis analysis.

SDS-PAGE. The proteins collected from 3 pmol of SNAs were analyzed by SDS-PAGE using a precast Mini Pro-TEAN TGX 4%-15% polyacrylamide gel (10 well, 50 µL, BioRad, CA, USA). Each sample was mixed with 2× Laemmli sample buffer (BioRad) at 1:1 ratio and loaded to the precast gel. Precision Plus Protein Dual Xtra Standards (BioRad) were used as a molecular weight marker. The gel was run for 1 h at 100 V in Tris-Glycine-SDS buffer. After rinsing the gel with 20% w/v NaCl solution (5 min) three times, the gel was then stained in 50 mL of Bio-Safe Coomassie Stain (BioRad, CA, USA) for 1 h at r.t. with gentle shaking. After that, the gel was destained in 100 mL of water for 1 h, and 20 mL of 20% w/v NaCl solution was added to the gel and left incubate for 2 h. The protein bands on the gel was visualized by ChemiDoc™ MP Imaging System (BioRad, CA, USA) in the red (Cy5) fluorescence channel with automatic exposure.

THP-1 macrophage surface marker labeling. To confirm that PMA treatment caused differentiation of THP-1 cells, a surface marker of macrophages, PE anti-human CD14 antibodies (mouse IgG1, κ; BioLegend, CA, USA), was used as a label. The labeling procedure follows the manufacturer's protocol. After labeling, the cell suspension was rinsed with PBS and then fixed for flow cytometry analysis in the PE channel. The distribution of PE fluorescence of the gated cells was collected, and the corresponding MFI values were calculated by FlowJo v10.

Figure 7:
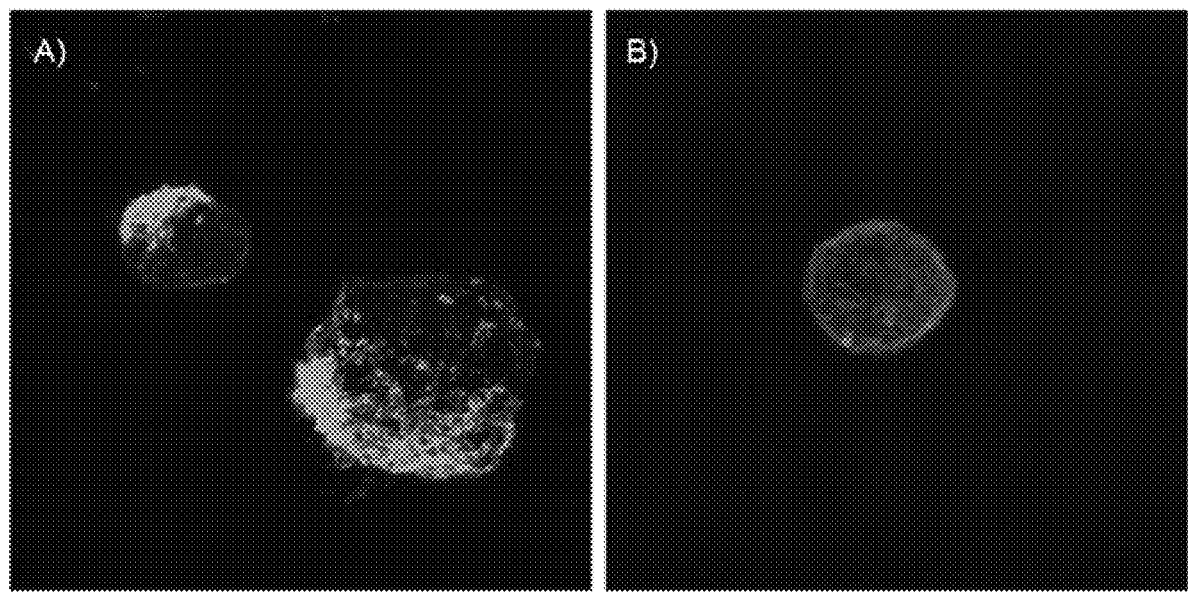
FIG. 7 shows the morphology of cytoskeleton with (A) and without (B) cytochalasin D treatment to the THP-1 macrophages. Cytoskeleton was stained with AF488 phalloidin.
Figure 8:
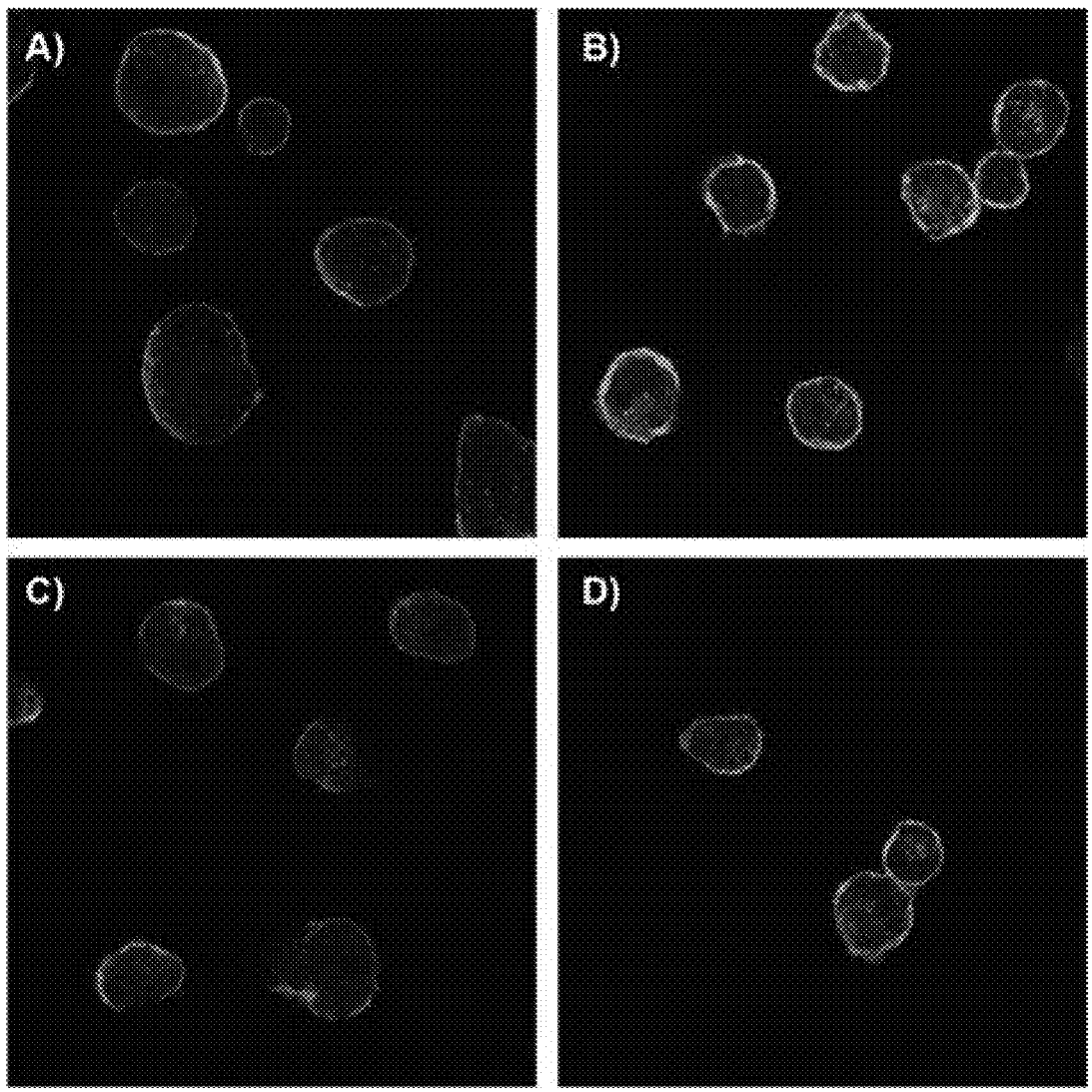
FIG. 8 shows an overlay of the SNA oligonucleotide shell (red) and cellular membrane (green) of the THP-1 macrophages pretreated with (A) and without cytochalasin D (B). (C) Overlay of the IgG-adsorbed SNA oligonucleotide shell and cellular membrane with cytochalasin D treatment. (D) IgG-adsorbed SNA oligonucleotide shell and cellular membrane without cytochalasin D treatment. Oligonucleotide shell was filled with 10% of Cy5-labeled DNA and cellular membrane was stained with Alexa 488-wheat germ agglutinin conjugates.

Confocal microscopy. To visualize the effect of cytochalasin D on actin disruption, fixed cells were stained with AlexaFluor 488 (AF488)-phalloidin (ThermoFisher, MA, USA) overnight at 4° C., rinsed with PBS for three times, and then mounted in an antifade mounting medium (ThermoFisher, MA, USA) for confocal imaging. To analyze the effects of actin de-polymerization on the location of SNAs, membrane of cells treated with and without cytochalasin D was stained with AF488-wheat germ agglutinin conjugates (WGA; ThermoFisher, MA, USA) following the manufacturer's protocol. All cells were imaged using a Zeiss LSM 800 (Carl Zeiss, Germany) with a 63× oil immersion objective. See FIGS. 7 and 8.

REFERENCES

1. Cedervall, T.; Lynch, I.; Lindman, S.; Berggård, T.; Thulin, E.; Nilsson, H.; Dawson, K. A.; Linse, S., Understanding the nanoparticle-protein corona using methods to quantify exchange rates and affinities of proteins for nanoparticles. *Proceedings of the National Academy of Sciences* 2007, 104 (7), 2050-2055.
2. Yan, Y.; Gause, K. T.; Kamphuis, M. M.; Ang, C. S.; O'Brien-Simpson, N. M.; Lenzo, J. C.; Reynolds, E. C.; Nice, E. C.; Caruso, F., Differential roles of the protein corona in the cellular uptake of nanoporous polymer particles by monocyte and macrophage cell lines. *ACS Nano* 2013, 7 (12), 10960-70.
3. Schöttler, S.; Becker, G.; Winzen, S.; Steinbach, T.; Mohr, K.; Landfester, K.; Mailänder, V.; Wurm, F. R., Protein adsorption is required for stealth effect of poly(ethylene glycol)- and poly(phosphoester)-coated nanocarriers. *Nat. Nanotechnol.* 2016, 11, 372.
4. Aoyama, M.; Hata, K.; Higashisaka, K.; Nagano, K.; Yoshioka, Y.; Tsutsumi, Y., Clusterin in the protein corona plays a key role in the stealth effect of nanoparticles against phagocytes. *Biochem Biophys Res Commun* 2016, 480 (4), 690-695.
5. Saha, K.; Rahimi, M.; Yazdani, M.; Kim, S. T.; Moyano, D. F.; Hou, S.; Das, R.; Mout, R.; Rezaee, F.; Mahmoudi, M.; Rotello, V. M., Regulation of Macrophage Recognition through the Interplay of Nanoparticle Surface Functionality and Protein Corona. *ACS Nano* 2016, 10 (4), 4421-30.
6. Schäffler, M.; Sousa, F.; Wenk, A.; Sitia, L.; Him, S.; Schleh, C.; Haberl, N.; Violatto, M.; Canovi, M.; Andreozzi, P.; Salmona, M.; Bigini, P.; Kreyling, W. G.; Krol, S., Blood protein coating of gold nanoparticles as potential tool for organ targeting. *Biomaterials* 2014, 35 (10), 3455-66.
7. Staufenbiel, S.; Weise, C.; Müller, R. H., Targeting of Intravenous Polymeric Nanoparticles by Differential Protein Adsorption. *Macromolecular Symposia* 2014, 345 (1), 42-50.
8. Salvati, A.; Pitek, A. S.; Monopoli, M. P.; Prapainop, K.; Bombelli, F. B.; Hristov, D. R.; Kelly, P. M.; Åberg, C.; Mahon, E.; Dawson, K. A., Transferrin-functionalized nanoparticles lose their targeting capabilities when a biomolecule corona adsorbs on the surface. *Nat. Nanotechnol.* 2013, 8, 137.
9. Jiang, X.; Weise, S.; Hafner, M.; Rocker, C.; Zhang, F.; Parak, W. J.; Nienhaus, G. U., Quantitative analysis of the protein corona on FePt nanoparticles formed by transferrin binding. *Journal of the Royal Society, Interface* 2010, 7 Suppl 1, S5-s13.
10. Tonigold, M.; Simon, J.; Estupinan, D.; Kokkinopoulou, M.; Reinholz, J.; Kintzel, U.; Kaltbeitzel, A.; Renz, P.; Domogalla, M. P.; Steinbrink, K.; Lieberwirth, I.; Crespy, D.; Landfester, K.; Mailander, V., Pre-adsorption of antibodies enables targeting of nanocarriers despite a biomolecular corona. *Nat Nanotechnol* 2018, 13 (9), 862-869.
11. Mirshafiee, V.; Mahmoudi, M.; Lou, K.; Cheng, J.; Kraft, M. L., Protein corona significantly reduces active targeting yield. *Chemical Communications* 2013, 49 (25), 2557-2559.
12. Lundqvist, M.; Stigler, J.; Elia, G.; Lynch, I.; Cedervall, T.; Dawson, K. A., Nanoparticle size and surface properties determine the protein corona with possible implications for biological impacts. *Proc Natl Acad Sci USA* 2008, 105 (38), 14265-70.
13. Ritz, S.; Schöttler, S.; Kotman, N.; Baier, G.; Musyanovych, A.; Kuharev, J.; Landfester, K.; Schild, H.; Jahn, O.; Tenzer, S.; Mailänder, V., Protein Corona of Nanoparticles: Distinct Proteins Regulate the Cellular Uptake. *Biomacromolecules* 2015, 16 (4), 1311-1321.
14. Liu, X.; Huang, N.; Li, H.; Jin, Q.; Ji, J., Surface and Size Effects on Cell Interaction of Gold Nanoparticles with Both Phagocytic and Nonphagocytic Cells. *Langmuir* 2013, 29 (29), 9138-9148.
15. García-Álvarez, R.; Hadjidemetriou, M.; Sánchez-Iglesias, A.; Liz-Marzán, L. M.; Kostarelos, K., In vivo 16. Dai, Q.; Yan, Y.; Ang, C.-S.; Kempe, K.; Kamphuis, M. M. J.; Dodds, S. J.; Caruso, F., Monoclonal Antibody-Functionalized Multilayered Particles: Targeting Cancer Cells in the Presence of Protein Coronas. *ACS Nano* 2015, 9 (3), 2876-2885.
17. Zhang, K.; Hao, L.; Hurst, S. J.; Mirkin, C. A., Antibody-linked Spherical Nucleic Acids for Cellular Targeting. *Journal of the American Chemical Society* 2012, 134 (40), 16488-16491.
18. Ogawara, K.-i.; Furumoto, K.; Nagayama, S.; Minato, K.; Higaki, K.; Kai, T.; Kimura, T., Pre-coating with serum albumin reduces receptor-mediated hepatic disposition of polystyrene nanosphere: implications for rational design of nanoparticles. *Journal of Controlled Release* 2004, 100 (3), 451-455.
19. Prozeller, D.; Pereira, J.; Simon, J.; Mailänder, V.; Morsbach, S.; Landfester, K., Prevention of Dominant IgG Adsorption on Nanocarriers in IgG-Enriched Blood Plasma by Clusterin Precoating. *Advanced Science* 2019, 0 (0), 1802199.
20. Mirkin, C. A.; Letsinger, R. L.; Mucic, R. C.; Storhoff, J. J., A DNA-based method for rationally assembling nanoparticles into macroscopic materials. *Nature* 1996, 382 (6592), 607-9.
21. Cutler, J. I.; Auyeung, E.; Mirkin, C. A., Spherical Nucleic Acids. *Journal of the American Chemical Society* 2012, 134 (3), 1376-1391.
22. Seferos, D. S.; Prigodich, A. E.; Giljohann, D. A.; Patel, P. C.; Mirkin, C. A., Polyvalent DNA Nanoparticle Conjugates Stabilize Nucleic Acids. *Nano Letters* 2009, 9 (1), 308-311.
23. Giljohann, D. A.; Seferos, D. S.; Daniel, W. L.; Massich, M. D.; Patel, P. C.; Mirkin, C. A., Gold Nanoparticles for Biology and Medicine. *Angewandte Chemie International Edition* 2010, 49 (19), 3280-3294.
24. Rosi, N. L.; Giljohann, D. A.; Thaxton, C. S.; Lytton-Jean, A. K. R.; Han, M. S.; Mirkin, C. A., Oligonucleotide-Modified Gold Nanoparticles for Intracellular Gene Regulation. *Science* 2006, 312 (5776), 1027-1030.
25. Massich, M. D.; Giljohann, D. A.; Seferos, D. S.; Ludlow, L. E.; Horvath, C. M.; Mirkin, C. A., Regulating Immune Response Using Polyvalent Nucleic Acid-Gold Nanoparticle Conjugates. *Molecular Pharmaceutics* 2009, 6 (6), 1934-1940.
26. Giljohann, D. A.; Seferos, D. S.; Prigodich, A. E.; Patel, P. C.; Mirkin, C. A., Gene Regulation with Polyvalent siRNA-Nanoparticle Conjugates. *Journal of the American Chemical Society* 2009, 131 (6), 2072-2073.
27. Jensen, S. A.; Day, E. S.; Ko, C. H.; Hurley, L. A.; Luciano, J. P.; Kouri, F. M.; Merkel, T. J.; Luthi, A. J.; Patel, P. C.; Cutler, J. I.; Daniel, W. L.; Scott, A. W.; Rotz, M. W.; Meade, T. J.; Giljohann, D. A.; Mirkin, C. A.; Stegh, A. H., Spherical Nucleic Acid Nanoparticle Conjugates as an RNAi-Based Therapy for Glioblastoma. *Science Translational Medicine* 2013, 5 (209), 209ra152-209ra152.
28. Elbakry, A.; Zaky, A.; Liebl, R.; Rachel, R.; Goepferich, A.; Breunig, M., Layer-by-layer assembled gold nanoparticles for siRNA delivery. *Nano Lett* 2009, 9 (5), 2059-64.
29. Ruan, W.; Zheng, M.; An, Y.; Liu, Y.; Lovejoy, D. B.; Hao, M.; Zou, Y.; Lee, A.; Yang, S.; Lu, Y.; Morsch, M.; Chung, R.; Shi, B., DNA nanoclew templated spherical nucleic acids for siRNA delivery. *Chemical Communications* 2018, 54 (29), 3609-3612.
30. Radovic-Moreno, A. F.; Chernyak, N.; Mader, C. C.; Nallagatla, S.; Kang, R. S.; Hao, L.; Walker, D. A.; Halo, T. L.; Merkel, T. J.; Rische, C. H.; Anantatmula, S.; Burkhart, M.; Mirkin, C. A.; Gryaznov, S. M., Immunomodulatory spherical nucleic acids. *Proceedings of the National Academy of Sciences* 2015, 112 (13), 3892-3897.
31. Wang, S.; Qin, L.; Yamankurt, G.; Skakuj, K.; Huang, Z.; Chen, P.-C.; Dominguez, D.; Lee, A.; Zhang, B.; Mirkin, C. A., Rational vaccinology with spherical nucleic acids. *Proceedings of the National Academy of Sciences* 2019, 201902805.
32. Molino, N. M.; Neek, M.; Tucker, J. A.; Nelson, E. L.; Wang, S.-W., Display of DNA on Nanoparticles for Targeting Antigen Presenting Cells. *ACS Biomaterials Science & Engineering* 2017.
33. Luo, X.; Li, Z.; Wang, G.; He, X.; Shen, X.; Sun, Q.; Wang, L.; Yue, R.; Ma, N., MicroRNA-Catalyzed Cancer Therapeutics Based on DNA-Programmed Nanoparticle Complex. *ACS Appl Mater Interfaces* 2017, 9 (39), 33624-33631.
34. Zhang, X.-Q.; Xu, X.; Lam, R.; Giljohann, D.; Ho, D.; Mirkin, C. A., Strategy for Increasing Drug Solubility and Efficacy through Covalent Attachment to Polyvalent DNA-Nanoparticle Conjugates. *ACS Nano* 2011, 5 (9), 6962-6970.
35. Prigodich, A. E.; Seferos, D. S.; Massich, M. D.; Giljohann, D. A.; Lane, B. C.; Mirkin, C. A., Nano-flares for mRNA Regulation and Detection. *ACS Nano* 2009, 3 (8), 2147-2152.
36. Seferos, D. S.; Giljohann, D. A.; Hill, H. D.; Prigodich, A. E.; Mirkin, C. A., Nano-flares: Probes for Transfection and mRNA Detection in Living Cells. *Journal of the American Chemical Society* 2007, 129 (50), 15477-15479.
37. Labib, M.; Mohamadi, R. M.; Poudineh, M.; Ahmed, S. U.; Ivanov, I.; Huang, C.-L.; Moosavi, M.; Sargent, E. H.; Kelley, S. O., Single-cell mRNA cytometry via sequence-specific nanoparticle clustering and trapping. *Nature Chemistry* 2018.
38. He, X.; Zeng, T.; Li, Z.; Wang, G.; Ma, N., Catalytic Molecular Imaging of MicroRNA in Living Cells by DNA-Programmed Nanoparticle Disassembly. *Angewandte Chemie International Edition* 2016, 55 (9), 3073-3076.
39. Yang, Y.; Huang, J.; Yang, X.; Quan, K.; Wang, H.; Ying, L.; Xie, N.; Ou, M.; Wang, K., FRET Nanoflares for Intracellular mRNA Detection: Avoiding False Positive Signals and Minimizing Effects of System Fluctuations. *Journal of the American Chemical Society* 2015, 137 (26), 8340-8343.
40. Chinen, A. B.; Guan, C. M.; Ko, C. H.; Mirkin, C. A., The Impact of Protein Corona Formation on the Macrophage Cellular Uptake and Biodistribution of Spherical Nucleic Acids. *Small* 2017, 13 (16), 1603847-n/a.
41. Chinen, A. B.; Ferrer, J. R.; Merkel, T. J.; Mirkin, C. A., Relationships between Poly(ethylene glycol) Modifications on RNA-Spherical Nucleic Acid Conjugates and Cellular Uptake and Circulation Time. *Bioconjugate Chemistry* 2016, 27 (11), 2715-2721.
42. Liu, B.; Liu, J., Freezing Directed Construction of Bio/Nano Interfaces: Reagentless Conjugation, Denser Spherical Nucleic Acids, and Better Nanoflares. *Journal of the American Chemical Society* 2017, 139 (28), 9471-9474.
43. Molina, M. A.; Codony-Servat, J.; Albanell, J.; Rojo, F.; Arribas, J.; Baselga, J., Trastuzumab (Herceptin), a Humanized Anti-HER2 Receptor Monoclonal Antibody, Inhibits Basal and Activated HER2 Ectodomain Cleavage in Breast Cancer Cells. *Cancer Research* 2001, 61 (12), 4744-4749.
44. Cai, R.; Chen, C., The Crown and the Scepter: Roles of the Protein Corona in Nanomedicine. *Adv Mater* 2018, e1805740.
45. Nguyen, V. H.; Lee, B.-J., Protein corona: a new approach for nanomedicine design. *International journal of nanomedicine* 2017, 12, 3137-3151.
46. Potter, E. V.; Stollerman, G. H., The opsonization of bentonite particles by gamma-globulin. *Journal of immunology* (Baltimore, Md.: 1950) 1961, 87, 110-118.
47. Daigneault, M.; Preston, J. A.; Marriott, H. M.; Whyte, M. K. B.; Dockrell, D. H., The Identification of Markers of Macrophage Differentiation in PMA-Stimulated THP-1 Cells and Monocyte-Derived Macrophages. *PLOS ONE* 2010, 5 (1), e8668.
48. Small, A.; Lansdown, N.; Al-Baghdadi, M.; Quach, A.; Ferrante, A., Facilitating THP-1 macrophage studies by differentiating and investigating cell functions in polystyrene test tubes. *Journal of Immunological Methods* 2018, 461, 73-77.
49. Furumoto, K.; Yokoe, J. I.; Ogawara, K. i.; Amano, S.; Takaguchi, M.; Higaki, K.; Kai, T.; Kimura, T., Effect of coupling of albumin onto surface of PEG liposome on its in vivo disposition. *International Journal of Pharmaceutics* 2007, 329 (1-2), 110-116.
50. Sobota, A.; Strzelecka-Kiliszek, A.; Gladkowska, E.; Yoshida, K.; Mrozińska, K.; Kwiatkowska, K., Binding of IgG-opsonized particles to FcγR is an active stage of phagocytosis that involves receptor clustering and phosphorylation. *Journal of Immunology* 2005, 175 (7), 4450-4457.
51. Choi, C. H.; Hao, L.; Narayan, S. P.; Auyeung, E.; Mirkin, C. A., Mechanism for the endocytosis of spherical nucleic acid nanoparticle conjugates. *Proc Natl Acad Sci USA* 2013, 110 (19), 7625-30.
52. Ahmed, M.; Baumgartner, R.; Aldi, S.; Dusart, P.; Hedin, U.; Gustafsson, B.; Caidahl, K., Human serum albumin-based probes for molecular targeting of macrophage scavenger receptors. *International journal of nanomedicine* 2019, 14, 3723-3741.
53. Frens, G., Controlled Nucleation for the Regulation of the Particle Size in Monodisperse Gold Suspensions. *Nature Physical Science* 1973, 241, 20.
54. Giljohann, D. A.; Seferos, D. S.; Patel, P. C.; Millstone, J. E.; Rosi, N. L.; Mirkin, C. A., Oligonucleotide Loading Determines Cellular Uptake of DNA-Modified Gold Nanoparticles. *Nano Letters* 2007, 7 (12), 3818-3821.
55. Docter, D.; Distler, U.; Storck, W.; Kuharev, J.; Wünsch, D.; Hahlbrock, A.; Knauer, S. K.; Tenzer, S.; Stauber, R. H., Quantitative profiling of the protein coronas that form around nanoparticles. *Nature Protocols* 2014, 9, 2030.

---

What is claimed is:

1. A spherical nucleic acid (SNA) comprising a protein corona, wherein the SNA comprises (i) a nanoparticle core and (ii) one or more oligonucleotides attached to the surface of the nanoparticle core; and
wherein the protein corona comprises a plurality of proteins, wherein each of the plurality of proteins is adsorbed on the surface of the SNA via a non-covalent interaction, and wherein the plurality of proteins comprises at least 5 proteins.

2. The SNA of claim 1, wherein the non-covalent interaction is an electrostatic interaction, a hydrogen bonding interaction, or a hydrophobic interaction.

3. The SNA of claim 1, wherein the plurality of proteins comprises from about 5 to about 50 proteins.

4. The SNA of claim 1, wherein the plurality of proteins comprises a targeting protein, a dysopsonin, a complement inhibitor, or a combination thereof.

5. The SNA of claim 4, wherein the dysopsonin is apolipoprotein E (ApoE), human serum albumin, immunoglobulin A (IgA), or a combination thereof.

6. The SNA of claim 4, wherein the complement inhibitor is fibrinogen, factor H, or a combination thereof.

7. The SNA of claim 4, wherein the targeting protein is transferrin.

8. The SNA of claim 4, wherein the targeting protein is an antibody, a cell-penetrating peptide, a nuclear localization signal peptide, or a combination thereof.

9. The SNA of claim 8, wherein the antibody is a human epidermal growth factor receptor 2 (HER2) antibody, an epidermal growth factor receptor (EGFR) antibody, a human TRAIL receptor 2 antibody, or a combination thereof.

10. The SNA of claim 1, wherein the nanoparticle core is a metallic core, a micellar core, a dendrimer core, a liposomal core, a polymer core, a metal-organic framework core, or a combination thereof.

11. The SNA of claim 10, wherein the polymer core comprises polylactide, a polylactide-polyglycolide copolymer, a polycaprolactone, a polyacrylate, alginate, polypyrrole, polythiophene, polyaniline, polyethylenimine, poly(methyl methacrylate), poly(lactic-co-glycolic acid) (PLGA), polystyrene, or chitosan.

12. The SNA of claim 1, wherein the one or more oligonucleotides is DNA, RNA, a modified form thereof, or a combination thereof.

13. The SNA of claim 1, wherein the one or more oligonucleotides comprises an inhibitory oligonucleotide.

14. The SNA of claim 13, wherein the inhibitory oligonucleotide is antisense DNA, small interfering RNA (siRNA), an aptamer, a short hairpin RNA (shRNA), a DNAzyme, or an aptazyme.

15. The SNA of claim 1, wherein the one or more oligonucleotides comprises an immunostimulatory oligonucleotide.

16. The SNA of claim 15, wherein the immunostimulatory oligonucleotide is double-stranded DNA (dsDNA).

17. The SNA of claim 15, wherein the immunostimulatory oligonucleotide is a toll-like receptor (TLR) agonist.

18. The SNA of claim 17, wherein the TLR agonist is a toll-like receptor 1 (TLR-1) agonist, toll-like receptor 2

(TLR-2) agonist, toll-like receptor 3 (TLR-3) agonist, toll-like receptor 4 (TLR-4) agonist, toll-like receptor 5 (TLR-5) agonist, toll-like receptor 6 (TLR-6) agonist, toll-like receptor 7 (TLR-7) agonist, toll-like receptor 8 (TLR-8) agonist, toll-like receptor 9 (TLR-9) agonist, toll-like receptor 10 (TLR-10) agonist, toll-like receptor 11 (TLR-11) agonist, toll-like receptor 12 (TLR-12) agonist, toll-like receptor 13 (TLR-13) agonist, or a combination thereof.

19. The SNA of claim 1, wherein the one or more oligonucleotides comprises a toll-like receptor (TLR) antagonist.

20. The SNA of claim 19, wherein the TLR-antagonist is a toll-like receptor 1 (TLR-1) antagonist, toll-like receptor 2 (TLR-2) antagonist, toll-like receptor 3 (TLR-3) antagonist, toll-like receptor 4 (TLR-4) antagonist, toll-like receptor 5 (TLR-5) antagonist, toll-like receptor 6 (TLR-6) antagonist, toll-like receptor 7 (TLR-7) antagonist, toll-like receptor 8 (TLR-8) antagonist, toll-like receptor 9 (TLR-9) antagonist, toll-like receptor 10 (TLR-10) antagonist, toll-like receptor 11 (TLR-11) antagonist, toll-like receptor 12 (TLR-12) antagonist, toll-like receptor 13 (TLR-13) antagonist, or a combination thereof.

21. A plurality of spherical nucleic acids (SNAs), each spherical nucleic acid (SNA) comprising a protein corona, wherein each SNA comprises (i) a nanoparticle core that is a metallic core, a micellar core, a liposomal core, a polymer core, a metal-organic framework core, or a combination thereof and (ii) one or more oligonucleotides attached to the surface of the nanoparticle core; wherein the protein corona comprises a plurality of proteins, wherein each of the plurality of proteins is adsorbed on the surface of each SNA via a non-covalent interaction, wherein the plurality of proteins comprises at least 5 proteins; and wherein the plurality of SNAs is monodisperse.

22. The plurality of SNAs of claim 21, wherein the plurality of SNAs has a mean diameter that is increased about 4 nanometers (nm) or more relative to a plurality of SNAs that does not comprise a protein corona.

\* \* \* \* \*

SEQUENCE LISTING

```
<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (20)..(20)
<223> OTHER INFORMATION: (SP18)2

<400> SEQUENCE: 1
tccatgagct tcctgagctt                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (20)..(20)
<223> OTHER INFORMATION: (SP18)2-SH

<400> SEQUENCE: 2
tttttttttt tttttttttt                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: CY3.5
```

```
<400> SEQUENCE: 3
aagctcagga agctcatgga                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: CY5
<220> FEATURE:
<221> NAME/KEY: misc_feature
<222> LOCATION: (20)..(20)
<223> OTHER INFORMATION: (SP18)2-SH

<400> SEQUENCE: 4
tttttttttt tttttttttt                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (20)..(20)
<223> OTHER INFORMATION: (SP18)2

<400> SEQUENCE: 5
tccatgacgt tcctgacgtt                                              20
```